(12) United States Patent
Al-Jaroudi et al.

(10) Patent No.: US 9,487,542 B1
(45) Date of Patent: Nov. 8, 2016

(54) MIXED LIGAND GOLD(III) COMPLEXES AND METHODS THEREOF

(71) Applicant: King Fahd University of Petroleum and Minerals, Dhahran (SA)

(72) Inventors: Said Al-Jaroudi, Qatif-Qudaih (SA); Muhammad Altaf, Dhahran (SA); Abdulaziz Al-Saadi, Dhahran (SA); Anvarhusein Abdulkadir Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/798,071

(22) Filed: Jul. 13, 2015

(51) Int. Cl.
*C07F 1/12* (2006.01)
*A61K 31/28* (2006.01)

(52) U.S. Cl.
CPC *C07F 1/12* (2013.01); *A61K 31/28* (2013.01)

(58) Field of Classification Search
CPC ........................................................ C07F 1/12
See application file for complete search history.

(56) References Cited

U.S. PATENT DOCUMENTS 7,635,776 B2   12/2009  Mashima et al.
8,895,611 B1   11/2014  Isab et al.

FOREIGN PATENT DOCUMENTS

JP    2002-241344 A     8/2002
WO    WO 2007/138545 A2  12/2007

OTHER PUBLICATIONS

Ito et al. "Absorption Spectra and Circular Dichroisms of Metal Complexes. I. Platinum(II)-, Palladium(II)- and Gold(III)-Complexes Containing Optically Active Diamines" Bulletin of the Chemical Society of Japan, 1967, pp. 2584-2891.*
Al-Jaroudi, et al. "Synthesis, spectroscopic characterization, electrochemical behavior and computational analysis of mixed diamine ligand gold (III) complexes: antiproliferative and in vitro cytotoxic evaluations against human cancer cell lines", Biometals, 2014, pp. 1115-1136.

* cited by examiner

*Primary Examiner* — Joseph Kosack
(74) *Attorney, Agent, or Firm* — Oblon, McClelland, Maier & Neustadt, L.L.P

(57) ABSTRACT

Gold(III) complexes having mixed ligands as anticancer agents. The atom is coordinated by bidentate ligands having diamino functional groups: a diaminocyclohexane ligand and an ethylenediamine ligand. These complexes can exist in both cis- and trans-configurations. Also described are pharmaceutical compositions incorporating the gold(III) complexes, methods of synthesis, methods of treating cancer and methods of inhibiting cancer cell proliferation and inducing cancer cell apoptosis.

14 Claims, 18 Drawing Sheets

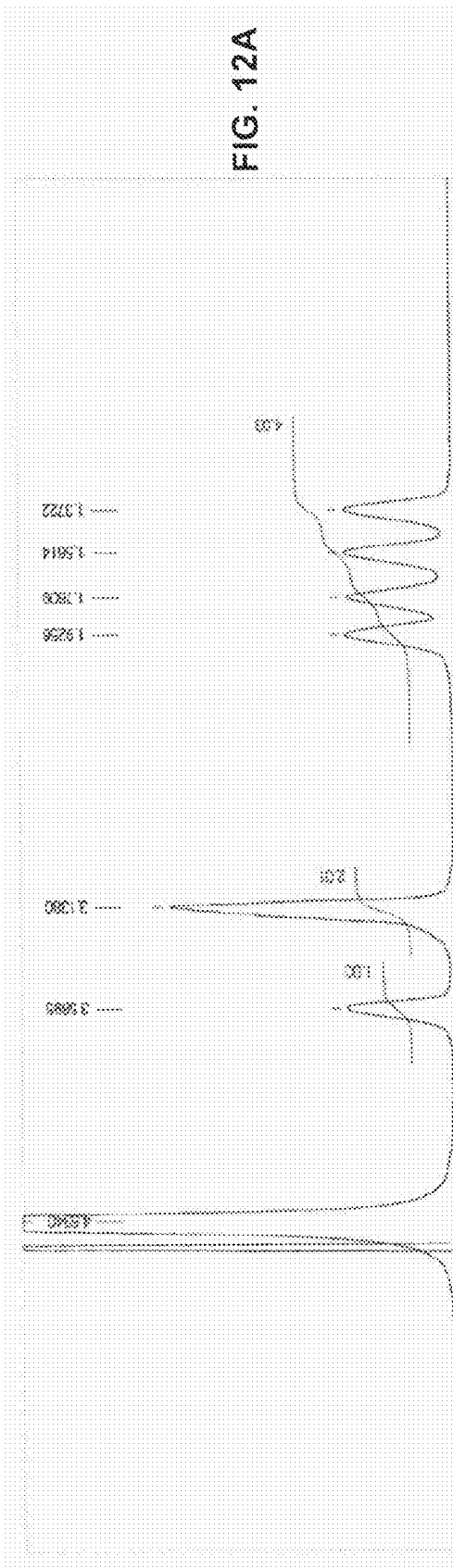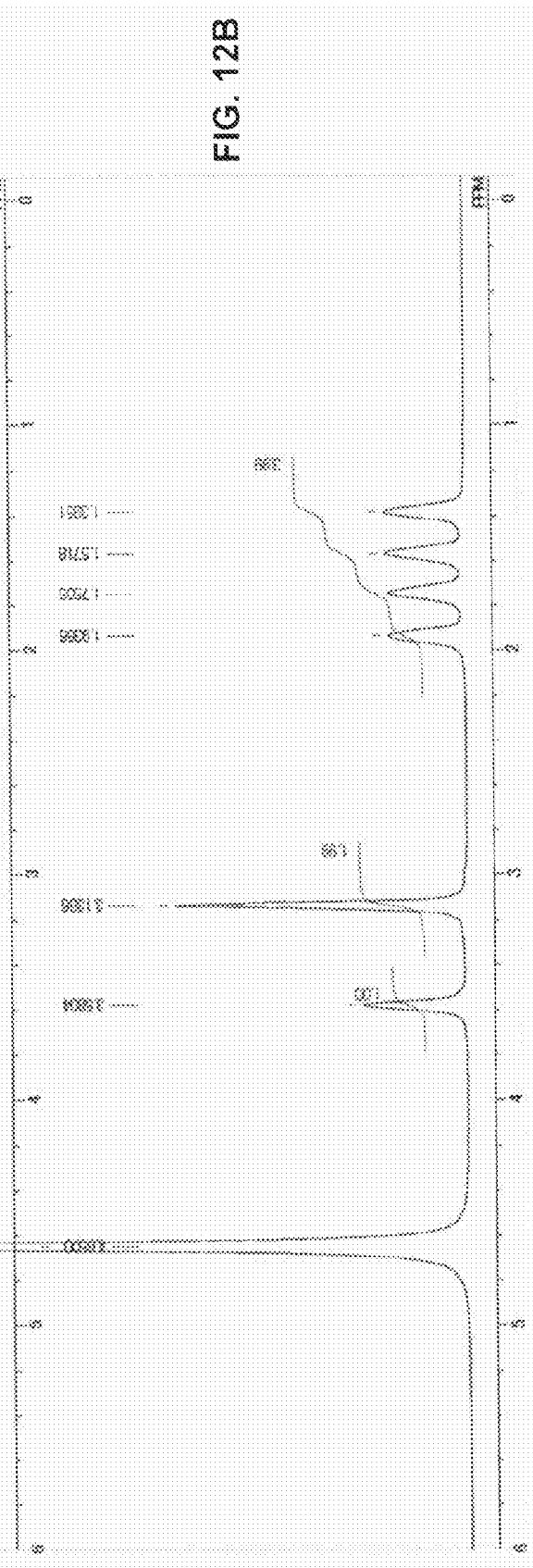

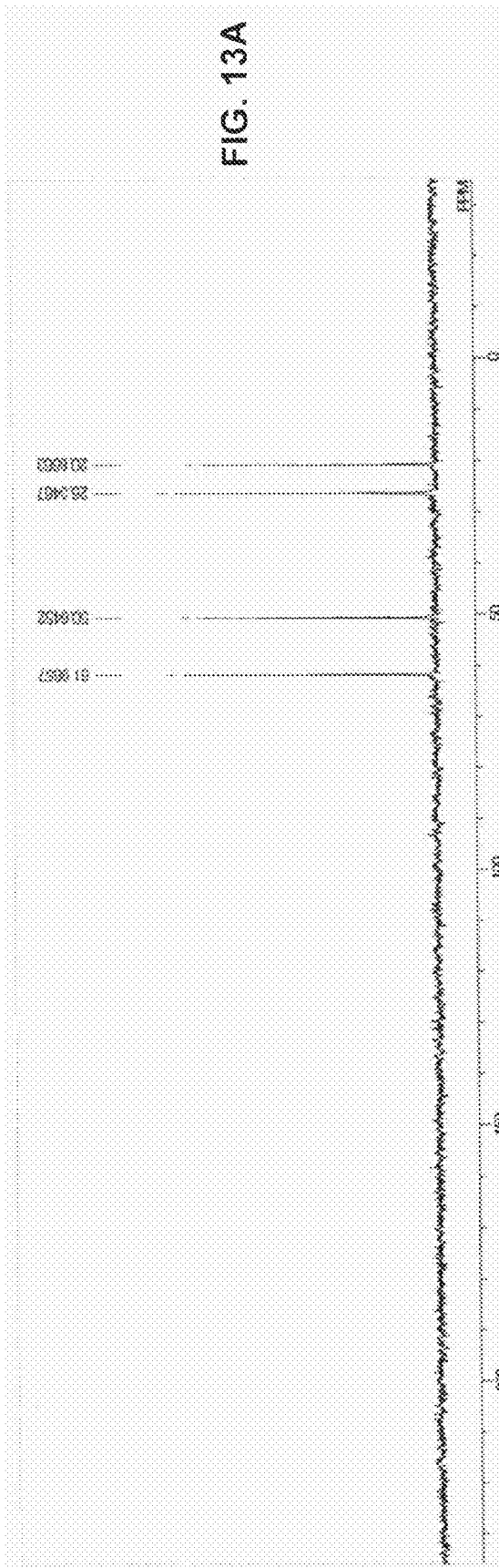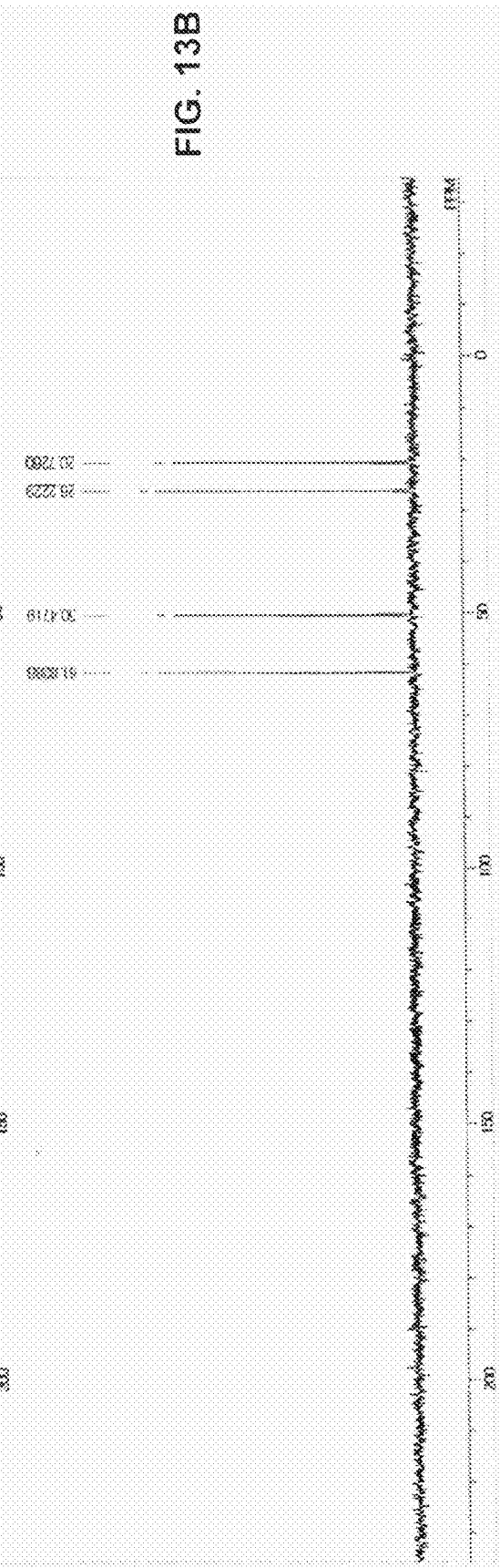

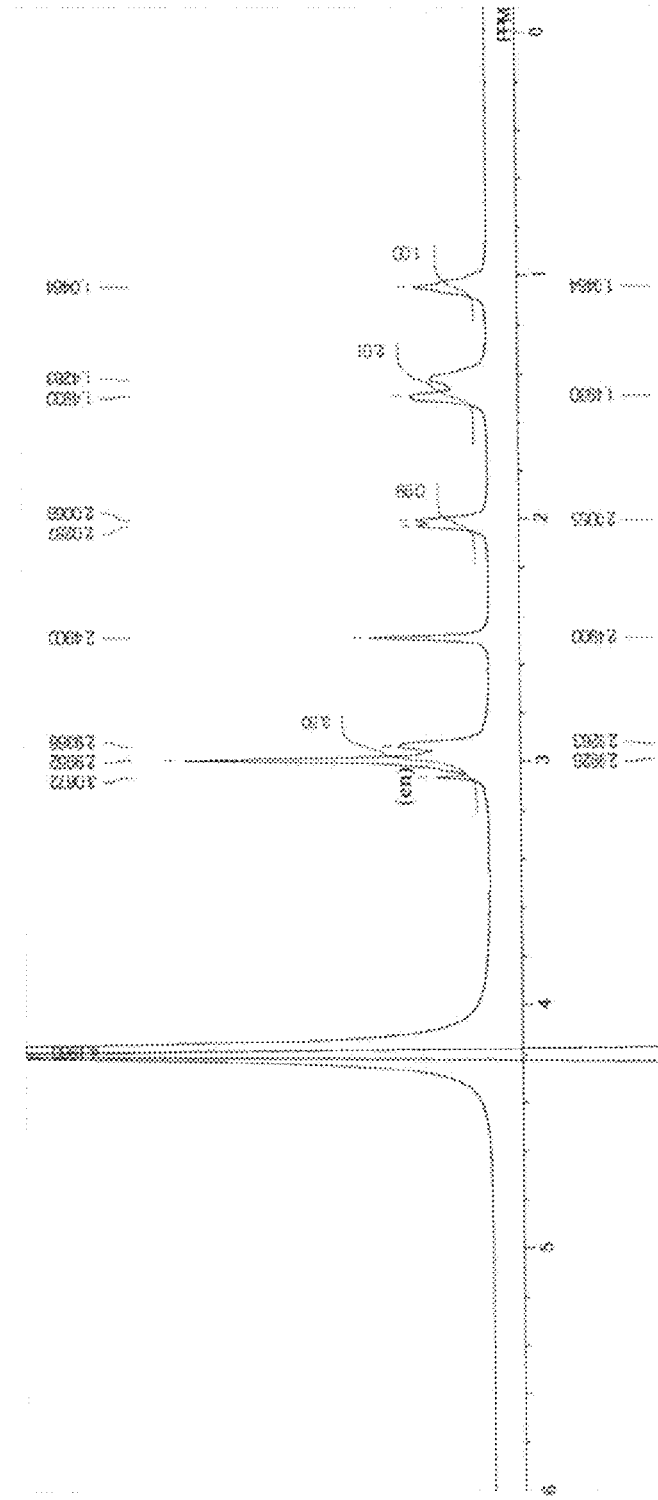
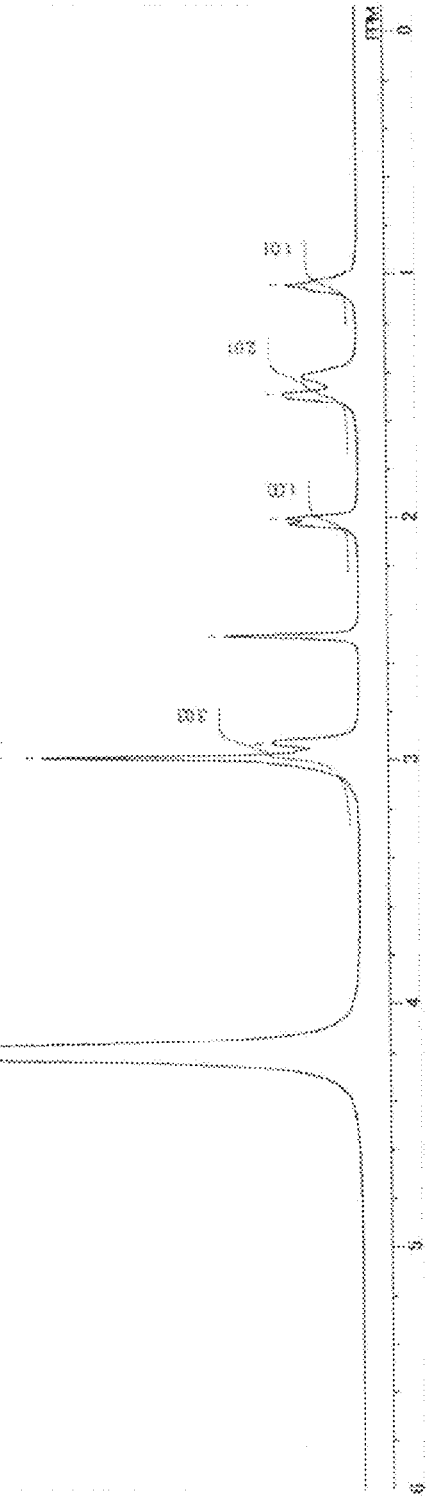
FIG. 14A
FIG. 14B

MIXED LIGAND GOLD(III) COMPLEXES AND METHODS THEREOF

STATEMENT OF FUNDING ACKNOWLEDGEMENT

This project was funded by the National Plan for Science, Technology and Innovation (MAARIFAH)—King Abdulaziz City for Science and Technology—the Kingdom of Saudi Arabia, award number (10-BIO1368-04).

BACKGROUND OF THE INVENTION

1. Technical Field

The present invention relates to pharmaceutical compounds. More particularly, the present invention relates to gold(III) complexes having mixed diamine ligands. The present invention includes the use of these gold(III) complexes for treatment of cancers and cell proliferative disorders.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The development of new metallodrugs with a pharmacological activity different from platinum drugs is one of the major goals of modern bioinorganic and bio-organometallic medicinal chemistry research [Jankovic S M, Djekovic A, Bugarcic Z D, Jankovic S V, Lukic G, Folic M, Canovic D (2012) Effects of aurothiomalate and gold(III) complexes on spontaneous motility of isolated human oviduct. Biometals 25:919-925; Arsenijevic N, Volarevic V, Milovanovic M, Bugarcic Z D (2013) Gold(III) complexes, cytotoxic effects. In: Kretsinger R H, Uversky V N, Permyakov E A (eds) Encyclopedia of metalloproteins, vol 2. Springer, Heidelberg, pp 922-927; Kouroulis K N, Hadjikakou S K, Kourkoumelis N, Kubicki M, Male L, Hursthouse M, Skoulika S, Metsios A K, Tyurin V Y, Dolganov A B, Milaeva E R, Hadjiliadis N (2009) Synthesis, structural characterization and in vitro cytotoxicity of new Au(III) and Au(I) complexes with thioamides. J Chem Soc Dalton Trans 47:10446-10456; Altaf M, Monim-ul-Mehboob M, Seliman A A, Isab A A, Dhuna V, Bhatia G, Dhuna K (2014) Synthesis, x-ray structures, spectroscopic analysis and anticancer activity of novel gold(I) carbene complexes. J Organomet Chem 765: 68-79; Hartinger C G, Dyson P J (2009) Bioorganometallic chemistry—from teaching paradigms to medicinal applications. Chem Soc Rev 38:391-401—each incorporated herein by reference in its entirety]. Among these non-platinum anticancer drugs, gold complexes have recently gained significant attention as a class of compounds with different pharmacodynamic and kinetic properties than cisplatin with strong cell growth inhibiting effects [Kouroulis K N, Hadjikakou S K, Kourkoumelis N, Kubicki M, Male L, Hursthouse M, Skoulika S, Metsios A K, Tyurin V Y, Dolganov A B, Milaeva E R, Hadjiliadis N (2009) Synthesis, structural characterization and in vitro cytotoxicity of new Au(III) and Au(I) complexes with thioamides. J Chem Soc Dalton Trans 47:10446-10456; Altaf M, Monim-ul-Mehboob M, Seliman A A, Isab A A, Dhuna V, Bhatia G, Dhuna K (2014) Synthesis, x-ray structures, spectroscopic analysis and anticancer activity of novel gold(I) carbene complexes. J Organomet Chem 765:68-79—each incorporated herein by reference in its entirety]. The cell growth inhibiting effects, in many cases, could be related to anti-mitochondrial effects that make the gold complexes interesting [Jankovic S M, Djekovic A, Bugarcic Z D, Jankovic S V, Lukic G, Folic M, Canovic D (2012) Effects of aurothiomalate and gold(III) complexes on spontaneous motility of isolated human oviduct. Biometals 25:919-925; Arsenijevic N, Volarevic V, Milovanovic M, Bugarcic Z D (2013) Gold(III) complexes, cytotoxic effects. In: Kretsinger R H, Uversky V N, Permyakov E A (eds) Encyclopedia of metalloproteins, vol 2. Springer, Heidelberg, pp 922-927; Kouroulis K N, Hadjikakou S K, Kourkoumelis N, Kubicki M, Male L, Hursthouse M, Skoulika S, Metsios A K, Tyurin V Y, Dolganov A B, Milaeva E R, Hadjiliadis N (2009) Synthesis, structural characterization and in vitro cytotoxicity of new Au(III) and Au(I) complexes with thioamides. J Chem Soc Dalton Trans 47:10446-10456—each incorporated herein by reference in its entirety].

Oxaliplatin, the so-called third generation of platinum (II) complex was synthesized as the most promising drug molecule in order to overcome the crossresistance experienced by cisplatin [Graham J, Mushin M, Kirkpatrick P (2004) Fresh from thepipeline oxaliplatin. Nat Rev Drug Discov 3(1):11-12—incorporated herein by reference in its entirety]. It bears a 1,2-diaminocyclohexane (1,2-DACH) ligand and oxalate as a leaving group. The bulky chiral ligand, 1R,2R-diaminocyclohexane (1R,2R-DACH), contributes to high cytotoxicity against cisplatin-resistant cell lines. It is possibly due to the steric hindrance effect of the 1,2-DACH-platinum—DNA adducts [Misset J L, Bleiberg H, Sutherland W, Bekradda M, Cvitkovic E (2000) Oxaliplatin clinical activity: a review. Crit Rev Oncol Hematol 35:75-93; Zdraveski Z Z, Mello J A, Farinelli C K, Essigmann J M, Marinus M G (2002) MutS preferentially recognizes cisplatin—over oxaliplatin—modified DNA. J Biol Chem 277:1255-1260—each incorporated herein by reference in its entirety]. In the same line, several substituted 1,2-DACH complexes have been evaluated for their cytotoxicity [Chaney S G (1995) The chemistry and biology of platinum complexes with the 1,2-diaminocyclohexane carrier ligand (review). Int J Oncol 6:1291-1305; Hoeschele J D, Showalter H D, Kraker A J, Elliott W L, Roberts B J, Kampf J W (1994) Synthesis, structural characterization, and antitumor properties of a novel class of large-ring platinum(II) chelate complexes incorporating the cis-1,4-diaminocyclohexane ligand in a unique locked boat conformation. J Med Chem 37:2630-2636—each incorporated herein by reference in its entirety]. Furthermore, a great number of Pt(II) complexes containing 1R,2R-DACH moiety have been synthesized and tested for anticancer activities against a panel of human cancer lines. A few of them have entered preclinical and clinical trials [Yu C W, Li K K, Pang S K, Au-Yeung S C, Ho Y P (2006) Anticancer activity of a series of platinum complexes integrating demethylcantharidin with isomers of 1,2-diaminocyclohexane. Bioorg Med Chem Lett 16:1686-1691; Yu Y, Lou L, Liu W, Zhu H, Ye Q, Chen X, Gao W, Hou S (2008) Synthesis and anticancer activity of lipophilic platinum(II) complexes of 3,5-diisopropylsalicylate. Eur J Med Chem 43:1438-1443—each incorporated herein by reference in its entirety]. Moreover, in search for better platinum(II) compounds, a wide variety of carrying ligands and leaving groups have been screened. Monti E, Gariboldi M, Maiocchi A, Marengo E, Cassino C, Gabano E, Osella D (2005) Cytotoxicity of platinum(ii) conjugate models. The effect of chelating arms and leaving groups on cytotoxicity: a QSAR approach. J Med Chem 48:857-866; Berger I, Nazarov A A, Hartinger C G, Groessl M, Valiandi S M, Jakupec M A, Keppler B K (2007), A glucose derivative as natural alternative to the cyclohexane-1,2-diamine ligand in the anticancer drug oxaliplatin. Chem Med Chem 2:505-514—each incorporated herein by reference in its entirety].

Gold(III) complexes, which are isoelectronic and isostructural to platinum(II) complexes, hold promise as possible anticancer agents [Chaves J D S, Neumann F, Francisco T M, Correa C C, Lopes M T P, Silva H, Fontes A P S, de Almeida M V (2014), Synthesis and cytotoxic activity of gold(I) complexes containing phosphines and 3-benzyl-1,3-thiazolidine-2-thione or 5-phenyl-1,3,4-oxadiazole-2-thione as ligands, Inorg Chim Acta 414:85-90; Cutillas N, Yellol G S, de Haro C, Vicente C, Rodriguez V, Ruiz J (2013), Anticancer cyclometalated complexes of platinum group metals and gold, Coord Chem Rev 257:2784-2797—each incorporated herein by reference in its entirety]. Surprisingly, only a few reports exist in the literature unfolding the cytotoxic properties and the in vivo anticancer effects of gold(III) complexes [van Rijt S H, Sadler P J (2009), Current applications and future potential for bioinorganic chemistry in the development of anticancer drugs, Drug Discov Today 14(23-24):1089-1097; Ronconi L, Marzano C, Zanello P, Corsini M, Miolo G, Macca C, Trevisan A, Fregona D (2006), Gold(III) dithiocarbamate derivatives for the treatment of cancer: solution chemistry, DNA binding, and hemolytic properties. J Med Chem 49:1648-1657—each incorporated herein by reference in its entirety]. Gold(III) complexes having the same square-planar geometries as cisplatin [Zou T, Lum C T, Chui S S, Che C-M (2013) Gold(III) complexes containing N-heterocyclic carbene ligalnds: thiol "Switchon" fluorescent probes and anti-cancer agents. Angew Chem 125:3002-3005; Cattaruzza L, Fregona D, Mongiat M, Ronconi M, Fassina A, Colombatti A, Aldinucci D (2011) Antitumor activity of gold(III)-dithiocarbamato derivatives on prostate cancer cells and xenografts. Int J Cancer 128(1):206-215—each incorporated herein by reference in its entirety], gold(III) complexes currently became the subject of profound anti-cancer research and hold great potential to enter clinical trials since some of them are highly cytotoxic to solid cancer tumors in vitro and in vivo while causing minimal systemic toxicity [Ronconi L, Aldinucci D, Dou Q P D (2010) Latest insights into the anticancer activity of gold(III)-dithiocarbamato complexes. Anticancer Agents Med Chem 10:283-292; Sun R W Y, Che C M (2009) The anti-cancer properties of gold(III) compounds with dianionic porphyrin and tetradentate ligands. Coord Chem Rev 253:1682-1691—each incorporated herein by reference in its entirety]. In general, gold(III) complexes are not very stable under physiological conditions due to their high reduction potential and fast hydrolysis rate. Therefore, the selection of a suitable ligand to enhance the stability is a challenge in the design of gold(III) complexes. Au(III) is most likely coordinated by at least two chelating nitrogen donors which lower the reduction potential of gold(III) center and by this means stabilize the complex [Giovagnini L, Ronconi L, Aldinucci D, Lorenzon D, Sitran S, Fregoni D J (2005) Synthesis, characterization, and comparative in vitro cytotoxicity studies of platinum(II), palladium(II), and gold(III) methylsarcosinedithiocarbamate complexes. J Med Chem 48:1588-1592; Casini A, Hartinger C, Gabbiani C, Mini E, Dyson P J, Keppler B K, Messori L (2008) Gold(III) compounds as anticancer agents: Relevance of gold—protein interactions for their mechanism of action. J Inorg Biochem 102:564-575—each incorporated herein by reference in its entirety] and facilitated extensive pharmacological investigation, both in vitro and in vivo [Tiekink E R T (2008) Anti-cancer potential of gold complexes. Inflammopharmacology 16:138-142; Casini A, Kelter G, Gabbiani C, Cinellu M A, Minghetti G, Fregona D, Fiebig H H, Messori L (2009) Chemistry, antiproliferative properties, tumor selectivity, and molecular mechanisms of novel gold(III) compounds for cancer treatment: a systematic study. J Biol Inorg Chem 14:1139-1149—each incorporated herein by reference in its entirety].

1,2-DACH ligand has structurally two asymmetric carbon centers, thus, 1,2-DACH can exist as three isomeric forms which includes two enantiomers (1R,2R-DACH) or (trans-1,2-DACH), (1S,2S-DACH) or (trans-1,2-DACH) and one diastereoisomer (1R,2S-DACH) or (cis-1,2-DACH). Since 1,2-DACH is chiral, the significance of stereochemical issues has been addressed by a number of investigators which affect the cytotoxicity of complexes containing 1,2-DACH [Kidani Y, Inagaki K, Saito R, Tsukagoshi S (1977) Synthesis and anti-tumor activities of platinum(II) complexes of 1,2-diaminocyclohexane isomers and their related derivatives. J Clin Hematol Oncol 7:197-202; Kemp S, Wheate N J, Buck D P, Nikac M, Collins J G, Aldrich-Wright J R (2007), The effect of ancillary ligand chirality and phenanthroline functional group substitution on the cytotoxicity of platinum(II)-based metallointercalators. J Inorg Biochem 101:1049-1058—each incorporated herein by reference in its entirety]. In spite of conflicting views [Gulloti M, Pasini A, Ugo R, Filippeschi S, Marmonti L, Spreafico F (1984) NMR coalescence effects resulting from stereochemical non-rigidity and halide exchange in octahedral rhodium(III) and iridium(III) tertiary phosphine complexes. Inorg Chim Acta 91:223-227; Noji M, Okamoto K, Kidani Y, Tashiro T (1981) Relation of conformation to antitumor activity of platinum(II) complexes of 1,2-cyclohexanediamine and 2-(aminomethyl)cyclohexylamine isomers against leukemia P388. J Med Chem 24:508-515; Pasini A, Velcich A, Mariani A (1982) Absence of diastereoisomeric behaviour in the interaction of chiral platinum anticancer compounds with DNA. Chem Biol Interact 42:311-320—each incorporated herein by reference in its entirety], the consensus is that the (R,R) isomer is generally more active than the (S,S) isomer [Burchenal J H, Kalaher K, O'Toole T, Chisholm J (1977), Lack of cross-resistance between certain platinum coordination compounds in mouse leukemia. Cancer Res 37:3455-3457; Bruck M A, Bau R, Noji M, Inagaki K, Kidani Y (1984), The crystal structures and absolute configurations of the antitumor complexes Pt(oxalato)(1R,2R-cyclohexanediamine) and Pt(malonato) (1R,2R-cyclohexanediamine). Inorg Chim Acta 92:279-284—each incorporated herein by reference in its entirety], although activity has also been demonstrated with the (R,S) isomer [Vollano J F, Al-Baker S, Dabrowiak J C, Schurig J E (1987) Comparative antitumor studies on platinum(II) and platinum(IV) complexes containing 1,2-diaminocyclohexane. J Med Chem 30:716-719—incorporated herein by reference in its entirety]. With regard to the stereochemistry of the complexes, Pt(II)(1R,2R-DACH) and Pt(II)(1S,2S-DACH) complexes have a higher anticancer activity than Pt(1R,2S-DACH) complex [Johnson N P, Butour J L, Villani G, Wimmer F L, Defais M, Pierson V, Brabec V (1989) Metal antitumor compounds: the mechanism of action of platinum complexes. Prog Clin Biochem Med 10:1-24—incorporated herein by reference in its entirety]. However, the analogous gold(III) compound, $[Au(en)_2]Cl_3$ has been reported to have higher anticancer activity than gold(III) (1R,2R-DACH) (trans-1,2-DACH) and gold(III) (1S,2S-DACH) (trans-DACH) [Isab A A, Shaikh M N, Monim-ul- Mehboob M, Al-Maythalony B A, Wazeer M I M, Altuwaijri S (2011) Synthesis, characterization and anti proliferative effect of [Au(en)$_2$]Cl$_3$ and [Au(N-propyl-en)$_2$]Cl$_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of [Au$_2$(pn)$_2$(Cl)$_2$]Cl$_2$.H$_2$O. Polyhedron 61:225-23; Al-Maythalony B A, Wazeer M I M, Isab A A (2009) Synthesis and characterization of gold(III) complexes with alkyldiamine ligands. Inorg Chim Acta 362:3109-3113; Al-Jaroudi S S, Fettouhi M, Wazeer M I M, Isab A A, Altuwaijri S (2013) Synthesis, characterization and cytotoxicity of new gold(III) complexes with 1,2-diaminocyclohexane: influence of stereochemistry on antitumor activity. Polyhedron 50:434-442; Al-Jaroudi S S, Monim-ul-Mehboob M, Altaf M, Fettouhi M, Wazeer M I M, Isab A A (2014) Synthesis, spectroscopic characterization, X-ray structure and electrochemistry of new bis(1,2-diaminocyclohexane) gold(III) chloride compounds and their anticancer activities against PC3 and SGC7901 cancer cell lines. New J Chem 38:3199-3211—each incorporated herein by reference in its entirety].

As in the case of the parent cisplatin, the anticancer activity of platinum(II)-1,2-DACH is accompanied by toxicity. The emergence of resistance, and low water solubility that can affect pharmacokinetics, are additional features that must be improved in the pursuit for a more effective material [Hanessian S, Wang J (1993) Hydrophilic analogs of (R, R)-diaminocyclohexane dichloroplatinum (DACH) and the influence of relative stereochemistry on antitumor activity. Can J Chem 71:2102-2108—incorporated herein by reference in its entirety]. In view of the foregoing, the present disclosure aims to provide gold(III) complexes having efficacy against a variety of cancers that also lack the severe toxic side effects associated with platinum-based drugs.

BRIEF SUMMARY OF THE INVENTION

According to a first aspect, the present disclosure relates to a gold(III) complex having Formula A:

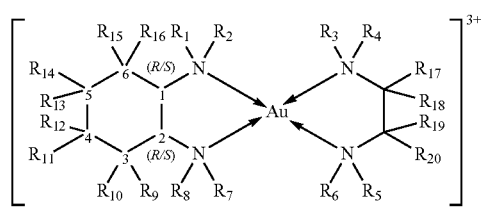

(Formula A)

or a pharmaceutically acceptable salt, ester, solvate or prodrug thereof. The complex has a cis- or trans-configuration. 1-6 each represents a carbon atom. $R_1$-$R_3$ are each independently selected from the group consisting of a hydrogen atom; a linear or branched, substituted or unsubstituted $C_1$-$C_8$ alkyl group; and a substituted or unsubstituted $C_6$-$C_8$ aryl group. $R_9$-$R_{20}$ are each independently selected from the group consisting of a hydrogen atom, a halogen atom, a hydroxyl group, a N-monosubstituted amino group, a N,N-disubstituted amino group, a substituted or unsubstituted $C_1$-$C_8$ alkyl group, a substituted or unsubstituted $C_1$-$C_8$ alkoxy group, a substituted or unsubstituted $C_3$-$C_8$ cycloalkyl group, and a substituted or unsubstituted $C_6$-$C_8$ aryl group.

In some embodiments, $R_1$-$R_8$ are each independently selected from the group consisting of a hydrogen atom, a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted neopentyl group, a substituted or unsubstituted sec-pentyl group, a substituted or unsubstituted tert-pentyl group, a substituted or unsubstituted n-hexane group, a substituted or unsubstituted isohexane group, and a substituted or unsubstituted neohexane group. $R_9$-$R_{20}$ are each independently a hydrogen atom, a halogen atom, a N-monosubstituted amino group, a N,N-disubstituted amino group, a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted neopentyl group, a substituted or unsubstituted sec-pentyl group, a substituted or unsubstituted tert-pentyl group, a substituted or unsubstituted n-hexane group, a substituted or unsubstituted isohexane group, and a substituted or unsubstituted neohexane group.

In certain embodiments, the gold(III) complex has a formula selected from the group consisting of Formula 1a, Formula 1b, Formula 2a and Formula 2b:

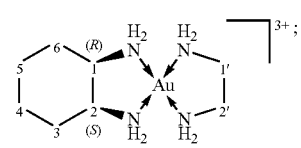

Formula 1a

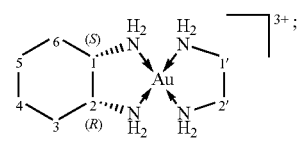

Formula 1b

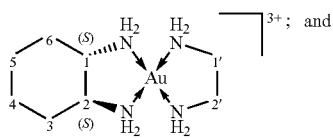

Formula 2a and

Formula 2b

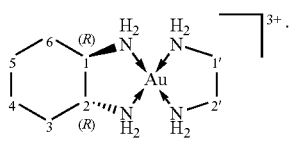

In one or more embodiments, the gold(III) complex further comprises one or more pharmaceutically acceptable anions selected from the group consisting of fluoride, chloride, bromide, iodide, nitrate, sulfate, phosphate, amide, methanesulfonate, ethanesulfonate, p-toluenesulfonate, salicylate, malate, maleate, succinate, tartarate, citrate, acetate, perchlorate, trifluoromethanesulfonate, acetylacetonate, hexafluorophosphate, and hexafluoroacetylacetonate.

According to a second aspect, the present disclosure relates to a composition comprising the gold(III) complex of according to the first aspect or a pharmaceutically acceptable salt, ester, solvate or prodrug thereof; and one or more pharmaceutically acceptable carriers.

In one embodiment, the composition further comprises one or more other active pharmaceutical agents.

In one embodiment, the composition is in solid, semi-solid or liquid dosage forms.

In one or embodiments, the composition is formulated for one or more modes of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

In a third aspect, the present disclosure is directed to a method for treating one or more types of cancer in a mammalian subject in need thereof. The method comprises administering a therapeutically effective amount of the composition of the second aspect to the mammalian subject.

In one embodiment, the one or more types of cancer are prostate cancer and/or gastrointestinal cancer.

In one embodiment, the therapeutically effective amount comprises 5-50 μM of the gold(III) complex or a pharmaceutically acceptable salt, ester, solvate or prodrug thereof.

In a fourth aspect, the present disclosure provides a method for inhibiting proliferation of cancer cells. The method comprise contacting the cancer cells with the gold (III) complex of the first aspect or a pharmaceutically acceptable salt, ester, solvate or prodrug thereof.

In at least one embodiment, the cancer cells are human cells.

In some embodiments, the cancer cells are prostate cancer cells and/or gastrointestinal cancer cells.

In some embodiments, the gold(III) complex has a concentration of 5-50 μM.

In one embodiment, the gold(III) complex exhibits an $IC_{50}$ of 1-20 μM for inhibiting the proliferation of the prostate cancer cells and/or the gastrointestinal cancer cells.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 12A and 12B are solution state $^1$H NMR spectra of [{(cis)-(+)-(1,2-DACH)}Au(en)]Cl$_3$ complex in D$_2$O at after 7 days and just after mixing, respectively.

FIGS. 13A and 13B are solution state $^{13}$C{$^1$H} NMR spectra of [{(cis)-(+)-(1,2-DACH)} Au(en)]Cl$_3$ complex in D$_2$O at after 7 days and just after mixing, respectively.

FIGS. 14A and 14B are solution state $^1$H NMR spectra of [{(S,S)-(+)-(1,2-DACH)}Au(en)]Cl$_3$ complex in D$_2$O at after 7 days and just after mixing, respectively.

DETAILED DESCRIPTION OF THE EMBODIMENTS

Figure 1A:
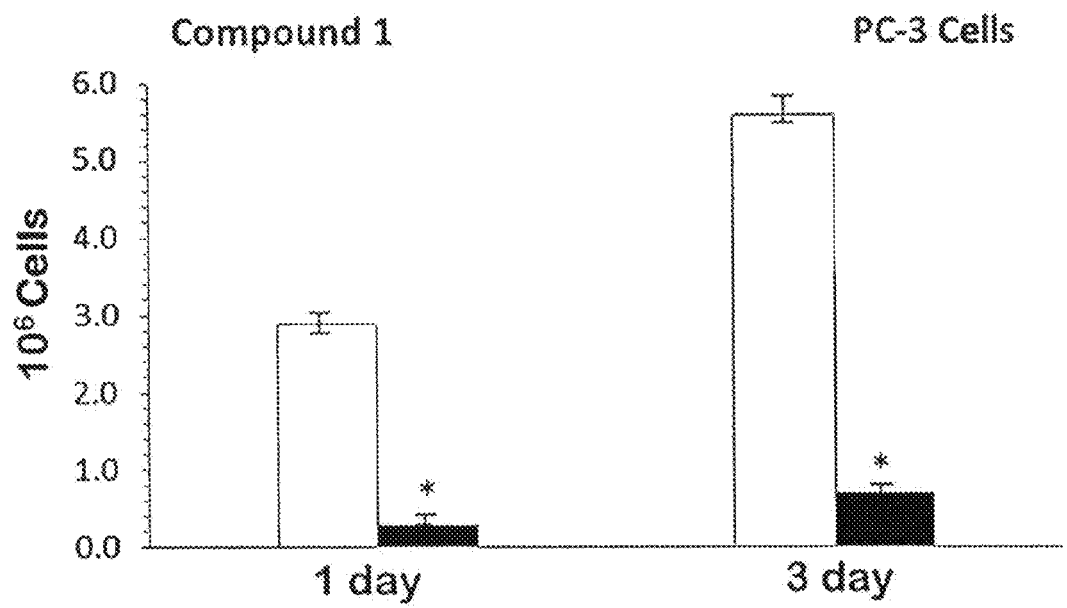
FIGS. 1A and 1B are bar graphs showing the time-dependent antiproliferative effect of 10 μM Compound 1 on PC3 and SGC7901 cells, respectively, for 24 and 72 h using MTT assay where results were expressed as the mean, SD, *P<0.05.
Figure 1B:
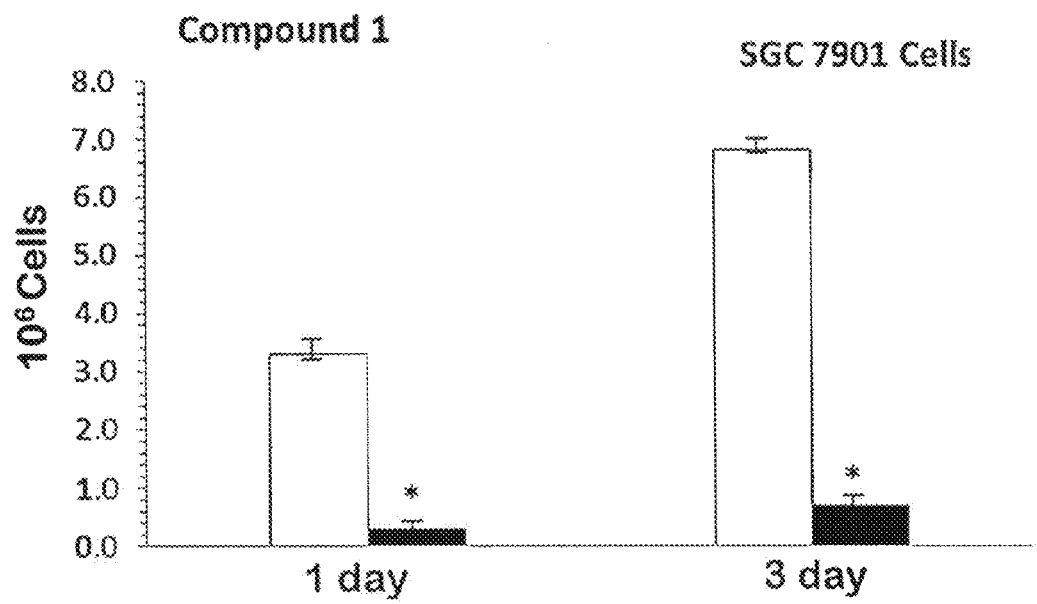
Figure 2A:
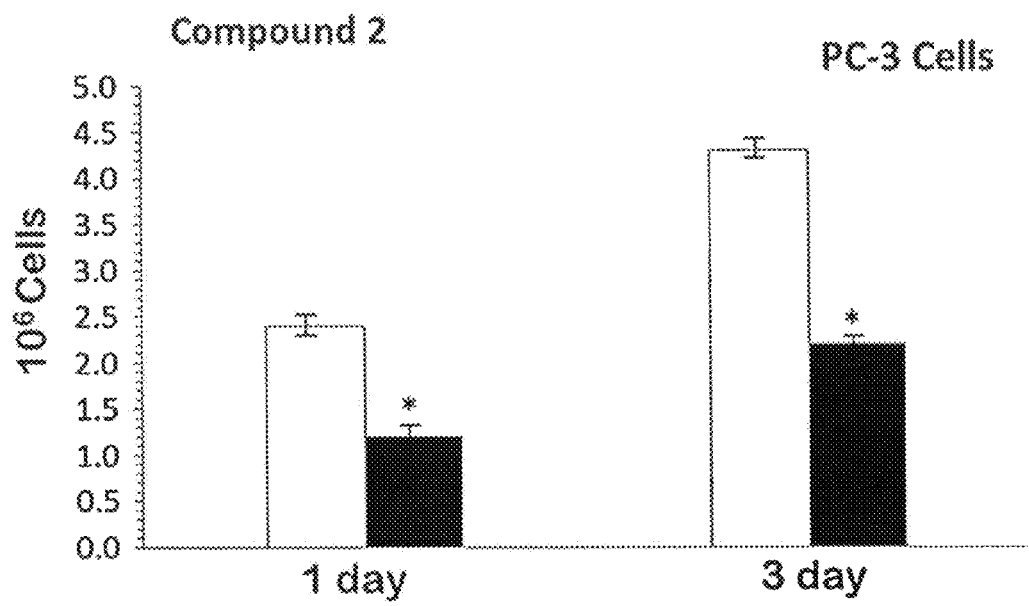
FIGS. 2A and 2B are bar graphs showing the time-dependent antiproliferative effect of 10 μM Compound 2 on PC3 and SGC7901 cells, respectively, for 24 and 72 h using MTT assay where results were expressed as the mean, SD, *P<0.05.
Figure 2B:
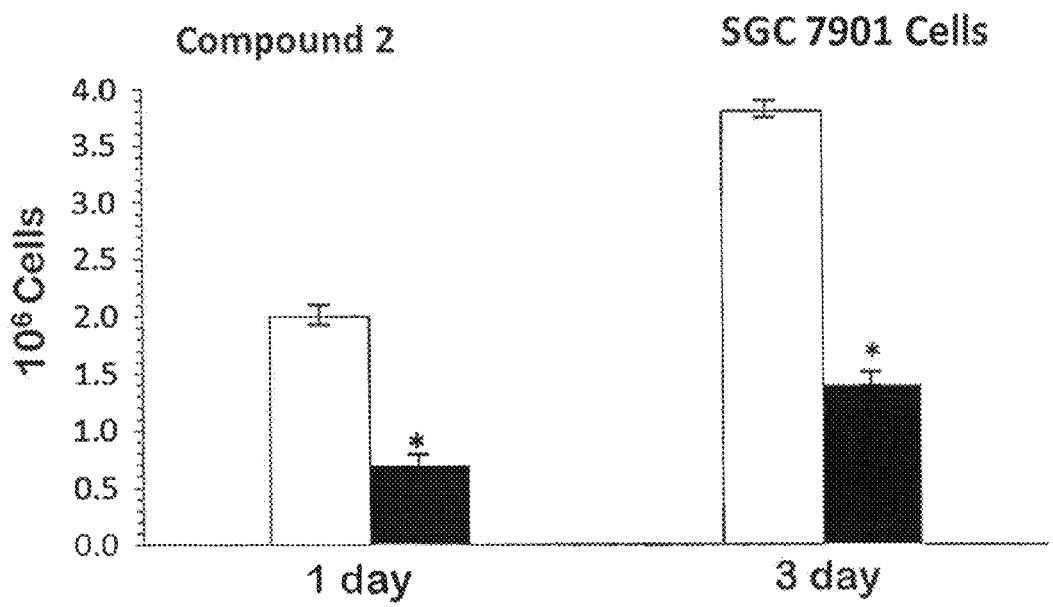
Figure 3A:
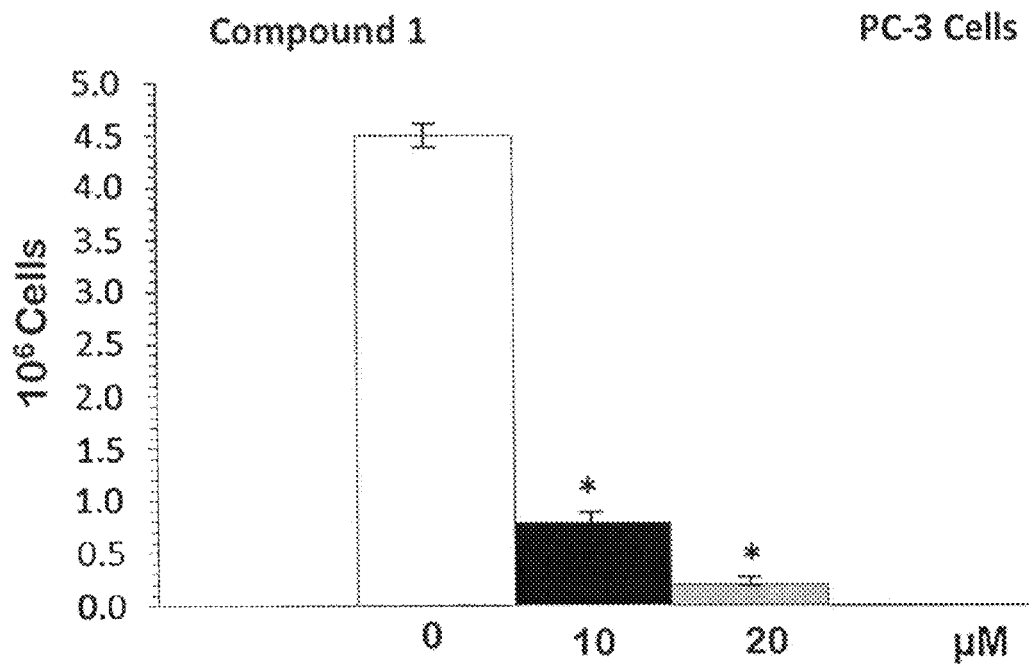
FIGS. 3A and 3B are bar graphs showing the time-dependent antiproliferative effect of 310 μM Compound 3 on PC3 and SGC7901 cells, respectively, for 24 and 72 h using MTT assay where results were expressed as the mean, SD, *P<0.05.
Figure 3B:
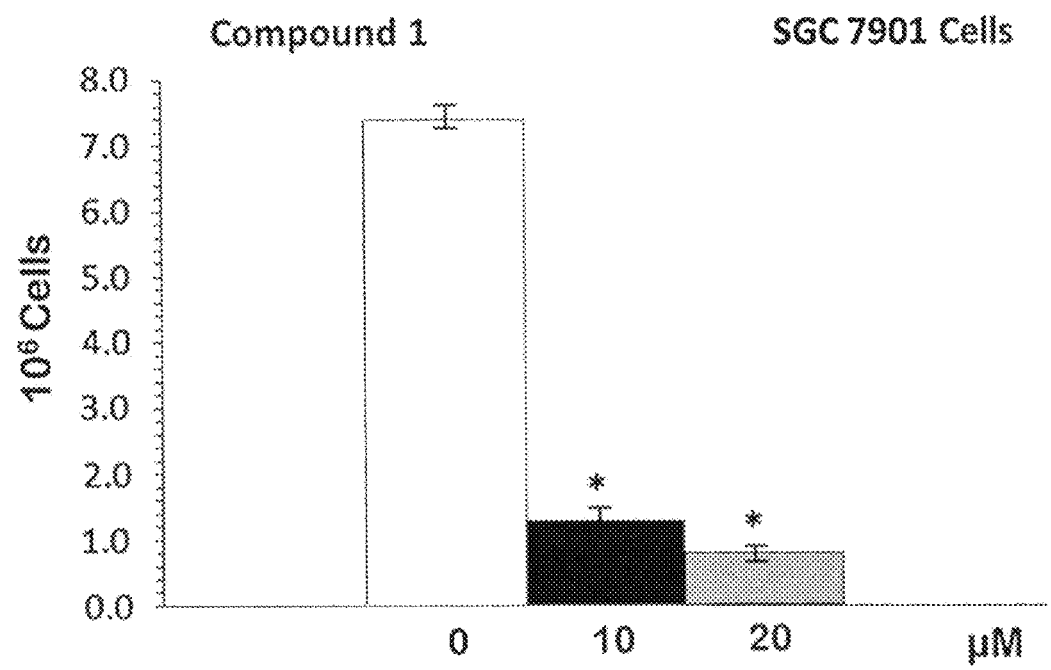

Referring now to the drawings, wherein like reference numerals designate identical or corresponding parts throughout the several views.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically C$_1$ to C$_8$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in viva. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.,* 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharma. Sci.,* 72(3): 324-325; Han, H. K. et al. (2000). Targeted prodrug design to optimize drug delivery, *AAPS PharmSci.,* 2(1): E6; Sadzuka Y. (2000). Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl 2:S15-27; Wang, W. et al. (1999) Prodrug approaches to the improved delivery of peptide drugs. *Curr. Pharm. Des.,* 5(4):265-87— each incorporated herein by reference in its entirety]. In some embodiments, "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the pharmaceutical composition refers to the combination of an active agent with a carrier, inert or active, making the composition especially suitable for diagnostic or therapeutic use in vivo or ex vivo.

"Pharmaceutically acceptable salt" or "pharmaceutically acceptable ester" refers to a compound in a pharmaceutically acceptable form such as an ester, a phosphate ester, a salt of an ester or a related) which, upon administration to a subject in need thereof, provides at least one of the gold(III) complexes described herein. Pharmaceutically acceptable salts and ester retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, alkaline earth metals such as calcium and magnesium, among numerous other acids well known in the art.

A "pharmaceutical composition" refers to a mixture of the compounds described herein or pharmaceutically acceptable salts, esters or prodrugs thereof, with other chemical components, such as physiologically acceptable carriers and excipients. One purpose of a pharmaceutical composition is to facilitate administration of at least one gold(III) complex to a subject.

As used herein, a "pharmaceutically acceptable carrier" or "pharmaceutically acceptable excipient" refers to a carrier or diluent that does not cause significant irritation to an organism and does not abrogate the biological activity and properties of the administered gold(III) complex. the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol (2) proteins such as gelatin and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The terms "including", "such as", "for example" and the like are intended to refer to exemplary embodiments and not to limit the scope of the present disclosure.

Gold(III) Complexes and Pharmaceutical Compositions Thereof

The present disclosure provides gold(III) complexes having medicinal or pharmaceutical properties, preferably antitumor, anticancer and/or antiproliferative properties. In these gold(III) complexes, each central gold(III) atom is coordinated, preferably chelated by two or more mixed or different ligands. Each ligand is diamine-based and contains two amino groups as functional groups. Specifically, the ligands are diaminocyclohexane and ethylenediamine with their base, unsubstituted structures shown below:

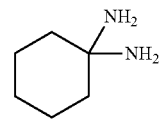

diaminocyclohexane

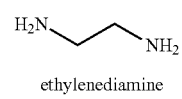

ethylenediamine

Both the diaminocyclohexane and ethylenediamine ligands as well as derivatives thereof bind to the central gold(III) atom in a bidentate manner. The nitrogen atoms in the diamino groups act as electron donor atoms that the gold(III) atom is coordinated. In other words, the gold(III) atom is coordinated to two donor nitrogen atoms from one diaminocyclohexane ligand and two donor nitrogen atoms from one ethylenediamine ligand. Accordingly, a gold(III) complex provided herein has a generic structure of, in cis-(1R,2S or 1S,2R) and trans-(1R,2R or 1S,2S) configurations:

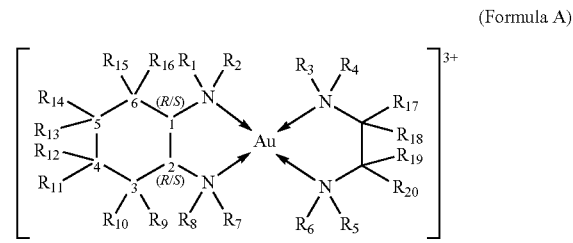

(Formula A)

where:

1-6 each represents a carbon atom;

$R_1$-$R_8$ are each independently a hydrogen; a linear or branched, substituted or unsubstituted $C_1$-$C_8$ alkyl group; or a substituted or unsubstituted $C_6$-$C_8$ aryl group; and $R_9$-$R_{20}$ are each independently selected from the group consisting of a hydrogen atom, a halogen atom, a hydroxyl group a N-monosubstituted amino group, a N,N-disubstituted amino group, a substituted or unsubstituted $C_1$-$C_8$ alkyl group, a substituted or unsubstituted $C_1$-$C_8$ alkoxy group a substituted or unsubstituted $C_3$-$C_8$ cycloalkyl group, and a substituted or unsubstituted $C_6$-$C_8$ aryl group.

In some embodiments, a gold(III) complex provided herein has a structure according to Formula A in cis-(1R,2S or 1S,2R) and trans-(1R,2R or 1S,2S) configurations, where:

$R_1$-$R_8$ are each independently a hydrogen; or a substituted or unsubstituted methyl, ethyl, propyl, isopropyl, n-butyl, isobutyl, sec-butyl group, tert-butyl, n-pentyl, neopentyl, sec-pentyl, tert-pentyl, n-hexane, isohexane, a neohexane group; and $R_9$-$R_{20}$ are each independently a hydrogen; a halogen; a N-monosubstituted amino group; a N,N-disubstituted amino group; or a substituted or unsubstituted methyl, ethyl, propyl, isopropyl, n-butyl, isobutyl, sec-butyl group, tert-butyl, n-pentyl, neopentyl, sec-pentyl, tert-pentyl, n-hexane, isohexane, a neohexane group.

In one embodiment, the gold(III) complex of the present disclosure is one of the following:

cis-(1R,2S)-(1,2-diaminocyclohexane)gold(III) ethylenediamine;

cis-(1S,2R)-(1,2-diaminocyclohexane)gold(III) ethylenediamine;

trans-(1R,2R)-(−)-(1,2-diaminocyclohexane)gold(III) ethylenediamine;

trans-(1S,2S)-(+)-(1,2-diaminocyclohexane)gold(III) ethylenediamine;

In one embodiment, the gold(III) complex of the present disclosure is according to one of the Formulas 1a, 1b, 2a and 2b:

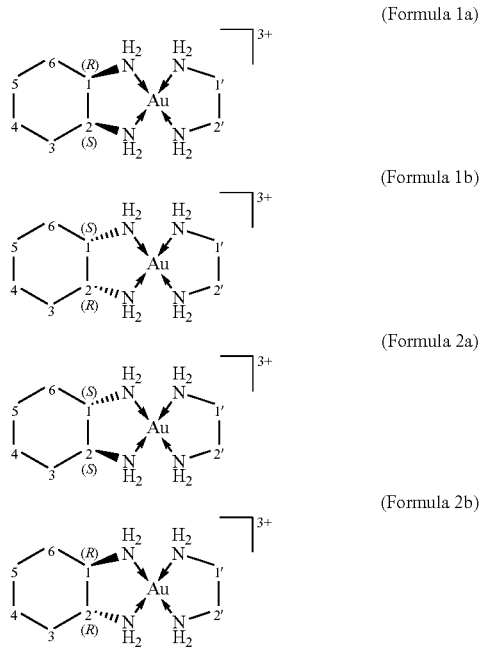

(Formula 1a)

(Formula 1b)

(Formula 2a)

(Formula 2b)

In certain embodiments, especially but not limited to pharmaceutical applications, the gold(III) complex can further include a counter-anion to form a pharmaceutically acceptable salt. As used herein, the term "counter-anion" refers to an anion, preferably a pharmaceutically acceptable anion that is associated with a positively charged gold(III) complex of at least one of the Formulas A, 1a, 1b, 2a and 2b. Non-limiting examples of pharmaceutically counter-anions include halides such as fluoride, chloride, bromide, iodide; nitrate; sulfate; phosphate; amide; methanesulfonate; ethanesulfonate; p-toluenesulfonate, salicylate, malate, maleate, succinate, tartarate; citrate; acetate; perchlorate; trifluoromethanesulfonate (triflate); acetylacetonate; hexafluorophosphate; and hexafluoroacetylacetonate. In some embodiments, the counter-anion is a halide, preferably chloride.

Another aspect of the present disclosure relates to pharmaceutical composition comprising one or more of the mixed diamine ligand gold(III) complexes described herein. In other words, the gold(IIII) complexes described herein or analogues or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of one or more of the gold(III) complexes described herein or derivatives thereof in combination with a pharmaceutically acceptable carrier and, in addition, may include other medicinal agents, pharmaceutical agents, carriers, diluents or other non-active ingredients. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

A mixed diamine ligand gold(III) complex of the present disclosure or an analogue or derivative thereof may be used in conjunction with one or more additional compounds, in the treatment or prevention of neoplasm; of tumor or cancer cell division, growth, proliferation and/or metastasis in a mammalian subject; induction of death or apoptosis of tumor and/or cancer cells; and/or any other form of proliferative disorder. A gold(III) complex of the present disclosure can be formulated as a pharmaceutical composition.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The mixed diamine ligand gold(III) complex of the present disclosure or the pharmaceutical composition thereof is especially effective in the treatment or prevention of colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

A pharmaceutical composition comprising one or more gold(III) complexes of the present disclosure can then be administered orally, systemically, parenterally, by inhalation spray, rectally, or topically in dosage unit formulations containing conventional nontoxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration such as transdermal patches or iontophoresis devices. The term parenteral as used herein includes intravesical, intradermal, transdermal, subcutaneous, intramuscular, intralesional, intracranial, intrapulmonal, intracardial, intrasternal and sublingual injections, or infusion techniques. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analogue or derivative thereof can be prepared by mixing the steroid or an analogue or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredients that can be combined with the carrier materials to produce a single dosage form varies depending upon the mammalian subject treated and the particular mode of administration.

Methods of Synthesis

The 1,2-(diaminocyclohexane)gold(III) ethylenediamine complexes of the present disclosure are not limited by their synthesis routes and methods. These gold(III) complexes can be prepared by various previously reported synthesis protocols with slight modifications as recognized as appropriate by a person of ordinary skill in the pharmaceutical and medicinal chemistry arts [U.S. Pat. No. 8,895,611; Al-Maythalony B A, Wazeer M I M, Isab A A (2009) Synthesis and characterization of gold(III) complexes with alkyl-diamine ligands. Inorg Chim Acta 362:3109-3113; Al-Jaroudi S S, Fettouhi M, Wazeer M I M, Isab A A, Altuwaijri S (2013) Synthesis, characterization and cytotoxicity of new gold(III) complexes with 1,2-diaminocyclohexane: influence of stereochemistry on antitumor activity. Polyhedron 50:434-442; Zhu S, Gorski W, Powell D R, Walmsley J A (2006) Synthesis, structures, and electrochemistry of gold(III) ethylenediamine complexes and interactions with guanosine 5'-monophosphate. Inorg Chem 45:2688-2694; Fernandez E J, Garcia-Luzuriaga E, Laguna A, Lopez-de-Luzuriaga, J M, Olmos, M E (2010) Synthesis of gold(III) complexes of 2-(diphenylthiophosphino)aniline; Casini A, Diawara, M C, Scopelliti R, Zakeeruddin S M, Gratzel M, Dyson P J (2010) Synthesis, characterization and biological properties of gold(III) compounds with modified bipyridine and bipyridylamine ligands. Dalton Trans. 39:2239-2245; Johnson M W, DiPasquale, A G, Bergman, R G, Toste, F D (2014) Synthesis of stable gold(III) pincer complexes with anionic heteroatom donors Organometallics 33:4169-4172; Moustatih A, Garnier-Suillerot A (1989) Bifunctional antitumor compounds: Synthesis and characterization of a gold(III)-streptonigrin complex with thiol-modulating properties. J. Med. Chem. 32:1426-1431—each incorporated herein by reference in its entirety].

In one embodiment, a gold(III) complex having a diaminecyclohexane ligand and a ethylenediamine ligand is prepared with equimolar amounts of a gold(III) precursor salt, ethylenediamine and a diaminocyclohexane [i.e. cis-(1R,2S)-(1,2-diaminocyclohexane), cis-(1S,2R)-(1,2-diaminocyclohexane), trans-(1R,2R)-(−)-(1,2-diaminocyclohexane) or trans-(1S,2S)-(+)-(1,2-diaminocyclohexane)gold (III) ethylenediamine including derivatives thereof]. Examples of the gold(III) salt include but are not limited to hydrated or anhydrous salts of sodium gold(III) chloride, potassium gold(III) chloride, gold(III) chloride, gold(III) oxide, gold(III) hydroxide, gold(III) bromide and gold(III) sulfide. The gold(III) precursor salt, the diaminocyclohexane and the ethylenediamine are dissolved separately in three portions of minimum ethanol or isopropyl alcohol at ambient temperature. Then, the gold(III) salt and diaminocyclohexane solutions are mixed, preferably dropwise, stirred briefly then filtered. The ethylenediamine solution is added to the filtered mixture, preferably dropwise and the diaminocyclohexane-gold(III)-ethylenediamine solution is stirred for at least overnight so that the final gold(III) complex product may be obtained as a white precipitate. The gold(III)

complex product is washed repeatedly and alternately with cold water, cold ethanol and then filtered and dried by heat or under reduced pressure in the presence of a dessicating agent such as but not limited to phosphorus pentoxide and silica gel.

Method of Inhibiting Proliferation of Cancer Cells and Inducing Cancer Cell Death The present disclosure further provides a method of inhibiting proliferation of human cancer cells and inducing apoptosis of the human cancer cells in vitro or in vivo. Human cancer cells are contacted with 1-100 μM of a gold(III) complex in accordance with the present disclosure or a composition comprising the gold(III) complex at the defined concentration range, preferably 2-75 μM, more preferably 5-50 μM, even more preferably 5-15 μM, 5-10 μM, 10-25 μM, 5-25 μM, 25-50 μM and 10-50 μM. The viability of cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay, Trypan Blue assay and TUNEL assay.

When contacted with one or more of the 1,2-(diaminocyclohexane)gold(III) ethylenediamine complexes at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

The half maximal inhibitory concentration ($IC_{50}$) values of the gold(III) complexes against the human cancer cells are no higher than 100 μM, preferably at least no higher than 50 μM, more preferably no higher than 30 μM, no higher than 20 μM, even more preferably no higher than 15 μM, no higher than 12 μM, most preferably no higher than 10 μM, no higher than 5 μM and no higher than 2 μM. In some embodiments, the $IC_{50}$ value of the gold (III) complexes against human prostate or gastric cancer cells, such as but not limited PC3 and SGC7901 cell lines, are ranged 1-20 μM, preferably 2-15 μM, more preferably 3-12 μM, even more preferably 4-10 μM. In some embodiments, compared to cisplatin, the $IC_{50}$ values of the gold(III) complexes provided herein are 0.5-5 times lower, preferably 0.5-3 times lower, more preferably 0.5-2 times lower, even more preferably 0.5-1 times lower.

In some embodiments, the human cancer cells are derived from commercial cell line models, including but are not limited to HeLa cervical cancer cells, A549 lung cancer cells, HCT-15 colon cancer cells, HCT-8 or HRT-8 colon cancer cells, DLD-1 colon cancer cells, MCF-7 breast cancer cells, A2780 ovarian cancer cells, A2780-cis cisplatin-resistant ovarian cancer cells, PC3 prostatic cancer cells, DU-145 prostatic cancer cells, SGC7901 gastrointestinal cancer cells and SGC7901—cis cisplatin-resistant gastrointestinal cancer cells.

In other embodiments, the human cancer cells are cancer cells of a human patient who has been diagnosed with, is suspected of having, or is susceptible to or at risk of having at least one form of cancer, preferably prostate cancer and/or gastrointestinal cancer.

Methods of Treating Cancers and Combination Therapies

Cancers such as but not limited to sarcomas, carcinomas, melanomas, myelomas, gliomas and lymphomas can be treated or prevented with the mixed diamine ligand gold(III) complexes provided herein. In some embodiments, methods incorporating the use of at least one of the gold(III) complexes of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more gold(III) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more gold(III) complexes of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more of gold(III) complexes or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more of gold(III) complexes or a pharmaceutical composition thereof may be administered in a single dose or multiple individual divided doses. In some embodiments, the interval of time between the administration of gold(III) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, mixed diamine ligand gold(III) compounds and one or more additional therapies are administered less than 1 day, 1 week, 2 weeks, 3 weeks, 4 weeks, one month, 2 months, 3 months, 6 months, 1 year, 2 years, or 5 years apart.

In certain embodiments, a gold(III) complex of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

EXAMPLES

The following examples have been included to further describe protocols for synthesizing and characterizing certain mixed diamine ligand gold(III) complexes (i.e. ethylenediamine and diaminocyclohexane ligands), and results thereof. It should be noted that these examples have been included for illustrative purposes, and are not intended to limit the scope of the appended claims.

In the following examples, the synthesized gold(III) complexes 1-3 containing ethylenediamine (en) and diaminocyclohexane (1,2-DACH) were characterized using elemental analyzer, solution and solid-state NMR measurements, UV-Vis, Mid- and Far-FTIR spectroscopic methods. The CHN analysis data support the formation of the mixed en and 1,2-DACH ligands gold(III) complexes 1-3 with general formula [(1,2-DACH)Au(en)]Cl$_3$. The spectroscopic methods and NMR measurements confirm the formation of gold(III) complexes containing bidentate en and 1,2-DACH ligands via N-donor atoms. The computational studies corroborate spectroscopic data of gold(III) complexes. The computational studies also demonstrate that trans-(1,2-DACH)-gold(III)-(en) isomer is slightly more stable than the cis-(1,2-DACH)-gold(III)-(en) isomer. The coordination sphere of these complexes around gold(III) center adopts distorted square planar geometry. According to antiproliferative effects of gold(III) complexes 1-3 on prostate (PC3) and gastric (SCG7901) cancer cells, the order of time dependent antiproliferative effect is complex 1 with cis-configuration>complex 3 with (1S,2S)(+)-configuration>complex 2 with trans-configuration for both PC3 and SGC7901 cancer cells. The comparative studies lead to the conclusion that complex 1 with cis-configuration of 1,2-DACH may be the most promising antiproliferative agent among mixed ligand based gold(III) complexes 1-3. The inhibitory effect of complexes 1-3 on the proliferation of rapidly dividing cells may be attributed to the induction of cell cycle blockage, interruption of the cell mitotic cycle, programmed cell death (apoptosis) or premature cell death (necrosis). The in vitro cytotoxicity results reveal that mixed diamine ligand gold(III) complexes are better anticancer agents than previously reported [Au(1,2-DACH)Cl$_2$]Cl, [Au(1,2-DACH)$_2$]Cl$_3$; and [Au(en)$_2$]Cl$_3$ and its derivative complexes against gastric SGC7901 cancer cell line.

Moreover, gold(III) complexes 1 and 3 were more effective than [Au(1,2-DACH)Cl$_2$]Cl against prostate PC3 cancer cells. The following examples prove the huge potential of mixed diamine ligand gold(III) complexes in the treatment of human prostate and gastric cancers. In particular, [(cis-1,2-DACH)Au(en)]Cl$_3$ makes a strong candidate as a potential chemopreventative and chemotherapeutic agent against human gastric cancer.

Example 1

Chemicals, cell lines and cell cultures Sodium tetrachloroaurate(III) dihydrate NaAuCl$_4$.2H$_2$O and ethylenediamine (en) were purchased from Sigma-Aldrich. cis-1,2-diaminocyclohexane cis-1,2-DACH (Formula X), trans-(±)-diaminocyclohexane trans-(±)-DACH (Formula Y), and (S,S)-(+)-diaminocyclohexane (S,S)-(+)-1,2-DACH (Formula Z) were purchased from Aldrich. Absolute C$_2$H$_5$OH, CH$_3$OH, D$_2$O and DMSO-d$_6$ were obtained from Fluka Chemicals Co. All other reagents as well as solvents were obtained from Aldrich Chemical Co., and used as received.

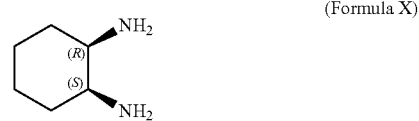

(Formula X)

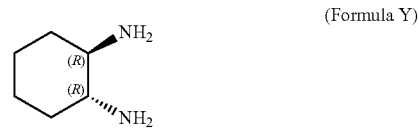

(Formula Y)

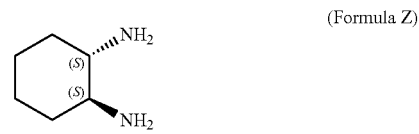

(Formula Z)

Human gastric SGC7901 cancer and prostate PC3 cancer cell lines were provided by American Type Culture Collection (ATCC). Cells were cultured in Dulbecco's Modified Eagle Medium (DMEM) supplemented with 10% fetal calf serum (FCS), penicillin (100 kU L$^{-1}$) and streptomycin (0.1 g L$^{-1}$) at 37° C. in a 5% CO$_2$-95% air atmosphere. MTT (3-(4,5-Dimethylthiazol-2-yl)-2,5-diphenyltetrazolium bromide, a yellow tetrazole) was purchased from Sigma Chemical Co, St. Louis, Mo., USA.

Example 2

Synthesis of Au(III) Complexes

Mixed ligand gold(III) chloride compounds namely cis-1,2-diaminocyclohexane ethylenediamine gold(III) chloride, [(en)Au{cis-(1,2-DACH)}]Cl$_3$ 1; trans-(±)-1,2-diaminocyclohexane ethylenediamine gold(III) chloride, [(en)Au{(trans-(±)-(1,2-DACH)}]Cl$_3$ 2; and (S,S)-(+)-1,2-diaminocyclohexane ethylenediamine gold(III) chloride [(en)Au{(S,S)-(+)-(1,2-DACH)}]Cl$_3$ 3; were synthesized by using one mole equivalent of Sodium aurate dihydrate NaAuCl$_4$.2H$_2$O with one mole of ethylenediamine (en) and one mole equivalent of cis-(1,2-DACH) or (trans-(±)-(1,2-DACH) or (S,S)-(+)-(1,2-DACH) respectively according to modification of the synthesis in the literature [Al-Maythalony B A, Wazeer M I M, Isab A A (2009) Synthesis and characterization of gold(III) complexes with alkyldiamine ligands. Inorg Chim Acta 362:3109-3113; Al-Jaroudi S S, Fettouhi M, Wazeer M I M, Isab A A, Altuwaijri S (2013) Synthesis, characterization and cytotoxicity of new gold(III) complexes with 1,2-diaminocyclohexane: influence of stereochemistry on antitumor activity. Polyhedron 50:434-442; Zhu S, Gorski W, Powell D R, Walmsley J A (2006) Synthesis, structures, and electrochemistry of gold(III) ethylenediamine complexes and interactions with guanosine 5'-monophosphate. Inorg Chem 45:2688-2694—each incorporated herein by reference in its entirety].

Sodium tetrachloroaurate dihydrate NaAuCl$_4$.2H$_2$O, 398 mg (1.0 mmol) was dissolved in minimum volume i.e. 10 mL of absolute ethanol at ambient temperature. In a separate beaker, 1,2-diaminocyclohexane (1,2-DACH), 114 mg (1.0 mmol) was dissolved in minimum volume i.e. 10 mL of absolute ethanol at ambient temperature. Both solutions were mixed dropwise and stirred for a half hour. Finally, a clear solution was obtained and filtered. In a separate beaker, ethylenediamine (en), 120 mg (1.0 mmol) is dissolved in minimum volume i.e. 10 mL of absolute ethanol at ambient temperature. The addition of (en) solution is added drop wise to the above filtered solution. Upon stirring for overnight, the white precipitate of [(en)Au(1,2-DACH)]Cl$_3$ was obtained. The product was isolated, dissolved in 2 mL of water and filtered through Celite pad to remove NaCl. Addition of 100 mL of cold CH$_3$OH to the filtrate and a white precipitate was obtained, filtered and washed with cold CH$_3$OH. The solid product was dried under reduced pressure with P$_2$O$_5$.

The yield of the compounds 1 (Formula 1a or 1b), 2 (Formula 2a or 2b) and 3 (Formula 3a or 3b) was in the range of 75-80%. Melting points and elemental analysis for complexes are presented in Table 1. The complexes prepared in the present study were characterized by FTIR and NMR measurements. The density functional calculations (DFC) studies based hybrid B3LYP is also performed to analyze the structures of gold(III) complexes. All the data support the formation of the desired [(1,2-DACH)Au(en)]Cl$_3$ complexes.

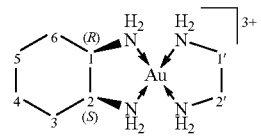

(Formula 1a)

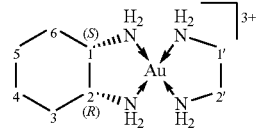

(Formula 1b)

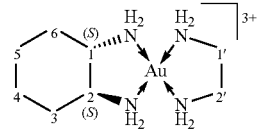

(Formula 2a)

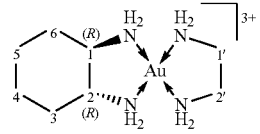

(Formula 2b)

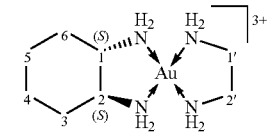

Formula 3

TABLE 1

Melting point (MP) and CHN analysis of gold complexes 1, 2 and 3.

| Complex | MP (° C.) | Found (calculated) % | | |
|---|---|---|---|---|
| | | H | C | N |
| (1) | 161-163 | 6.57 (6.64) | 22.26 (22.59) | 13.05 (13.17) |
| (2) | 175-178 | 6.59 (6.64) | 22.32 (22.59) | 13.01 (13.17) |
| (3) | 176-178 | 6.60 (6.64) | 22.48 (22.59) | 13.03 (13.17) |

Example 3

Electronic Spectra

Electronic spectra where obtained for the gold(III) complexes using Lambda 200, Perkin-Elmer UV-Vis spectrometer. UV-Vis spectroscopy was used to determine the stability of the complexes in a physiological buffer (40 mM phosphate, 4 mM NaCl, pH 7.4). Electronic spectra were recorded on freshly prepared of each complex in buffer solution at room temperature. Then, their electronic spectra were monitored over 7 days at 37° C. The resulting UV-Vis absorption data are shown in Table 2.

TABLE 2

$\lambda_{max}$ values derived from UV-Vis spectra for Au(III) complexes 1, 2 and 3.

| Complex | $\lambda_{max}$ (nm) |
|---|---|
| NaAuCl$_4$•2H$_2$O | 293 |
| (1) | 335 |
| (2) | 338 |
| (3) | 339 |

Example 4

Mid and Far-IR Studies

The solid-state FTIR spectra of the free ligands (1,2-DACH and en) and their corresponding mixed ligand gold (III) complexes were recorded on a Perkin-Elmer FTIR 180 spectrophotometer using KBr pellets over the range 4,000-400 cm$^{-1}$. The selected mid-FTIR frequencies of free ligands and corresponding mixed ligands gold(III) complexes are given in Table 3. Far infrared spectra were recorded for compounds 1, 2 and 3 at 4 cm$^{-1}$ resolution at room temperature as cesium chloride (CsCl) disks on a Nicolet 6700 FTIR with far-FTIR beam splitter. The selected far-FTIR data for free ligands and their corresponding mixed ligand gold(III) complexes are given in Table 4. The references cited in Tables 3 and 4 are Wadt W R, Hay P J (1985b) Ab initio effective core potentials for molecular calculations. Potentials for main group element Na to Bi. J Chem Phys 82:284-298; Hartinger C G, Dyson P J (2009) Bioorganometallic chemistry—from teaching paradigms to medicinal applications. Chem Soc Rev 38:391-401; and Wadt W R, Hay P J (1985c) Ab initio effective core potentials for molecular calculations. Potentials for K to Au including the outermost core orbitals. J Chem Phys 82:299-305, which are incorporated herein by reference in their entireties.

TABLE 4

Far-FTIR frequencies, $\nu(cm^{-1})$ for the mixed ligand Au(III) complexes 1, 2 and 3.

| Complex | Au—Cl | Au—N | Refs. |
|---|---|---|---|
| NaAuCl$_4$•2H$_2$O | 365 | — | This work |
| [(en)AuCl$_2$]Cl | — | 391, 474 | Wadt and Hay (1985c) |
| [cis-(1,2-DACH)AuCl$_2$]Cl | 352, 367 | 437 | Hartinger and Dyson (2009) |
| (1) | — | 326, 417 | This work |
| [trans-(±)-(1,2-DACH)AuCl$_2$]Cl | 353, 365 | 437 | Hartinger and Dyson (2009) |
| (2) | — | 391, 442 | This work |
| [(S,S)-(+)-(1,2-DACH)AuCl$_2$]Cl | 353, 366 | 395, 436 | Hartinger and Dyson (2009) |
| (3) | — | 376, 440 | This work |

Example 5

Solution NMR Measurements

All NMR measurements were carried out on a Jeol JNM-LA 500 NMR spectrophotometer at 298 K. The $^1$H NMR spectra were recorded at a frequency of 500.00 MHz. The $^{13}$C NMR spectra were obtained at a frequency of 125.65 MHz with $^1$H broadband decoupling. The spectral conditions were: 32 k data points, 0.967 s acquisition time, 1.00 s pulse delay and 45 pulse angle. The chemical shifts are referenced to 1,4-dioxane as an internal standard in 13C NMR measurements. The $^1$H and $^{13}$C NMR spectra chemical shifts are given in Tables 5 and 6, according to Formulas 1a-b, 2a-b and 3a-b.

TABLE 3

Mid-FTIR frequencies, $\nu(cm^{-1})$ for the mixed ligand Au(III) complexes 1, 2 and 3.

| Complex | $\nu$(N—H) | $\nu_{shift}$ | $\nu$(C—N) | $\nu_{shift}$ | Refs. |
|---|---|---|---|---|---|
| en | 3.393 w | | 1.033 m | | Wadt and Hay (1985b) |
| [(en)AuCl$_2$]Cl | 3.422 br | 29 | 1.045 m | 12 | Wadt and Hay (1985b) |
| cis-(1,2-(DACH) | 3.356 m, 3.286 m | | 1.092 s | | Hartinger and Dyson (2009) |
| [{cis-(1,2-DACH)}AuCl$_2$]Cl | 3.414 w | 93 | 1.183 m | 91 | Hartinger and Dyson (2009) |
| (1) | 3.395 br | 74$^a$, 2$^b$ | 1.182 m | 90$^a$, 149$^b$ | This work |
| trans-(±)-(1,2-DACH) | 3.348 m. 3,271 m 3.183 m | | 1.082 m | | Hartinger and Dyson (2009) |
| [{trans-(±)-(1,2-DACH)}AuCl$_2$]Cl | | 137, 149, 201 | 1.175 m | 93 | Hartinger and Dyson (2009) |
| (2) | 3.432 br | 168$^a$, 39$^b$ | 1.180 m | 93$^a$, 147$^b$ | This work |
| (S,S)-(+)-(1,2-DACH) | 3.340 m, 3.251 m, 3.167 m | | 1.082 m | | Hartinger and Dyson (2009) |
| [{S,S-(+)-(1,2-DACH)}AuCl$_2$]Cl | | | 1.171 m | 89 | Hartinger and Dyson (2009) |
| (3) | 3.386 br | 132$^a$, −7$^b$ | 1.180 m | 98$^a$, 147$^b$ | This work |

$^a$With respect to (DACH)
$^b$With respect to (en)

TABLE 5

$^1$H NMR chemical shifts of free ligands and complexes 1, 2 and 3 in D$_2$O.

| | $^1$H (δ in ppm) | | | | | | |
|---|---|---|---|---|---|---|---|
| Compound | H1, H2 | H3, H6 (eq) | H3, H6 (ax) | H4, H5 (eq) | H4, H5 (ax) | H1', H2' | Refs. |
| en | — | — | — | — | — | 3.2, s | This work |
| cis-(1,2-DACH) | 2.23, m | 1.85, m | 1.69, m | 1.28, m | 1.12, m | — | Hartinger and Dyson (2009) |
| (1) | 3.61, m | 1.96, m | 1.77, m | 1.59, m | 1.41, m | 3.16, s | This work |
| trans-(±)-(1,2-DACH) | 2.25, m | 1.85, m | 1.68, m | 1.28, m | 1.11, m | — | Hartinger and Dyson (2009) |
| (2) | 3.05, m | 2.11, m | 1.54, m | 1.48, m | 1.10, m | 3.14, s | This work |
| (S,S)-(+)-(1,2-DACH) | 2.24, m | 1.85, m | 1.69, m | 1.28, m | 1.11, m | — | Hartinger and Dyson (2009) |
| (3) | 3.08, m | 2.19, m | 1.63, m | 1.54, m | 1.19, m | 3.17, s | This work |

TABLE 6

Solution-state $^{13}$C NMR chemical shifts of free ligands and complexes 1, 2 and 3 in D$_2$O.

| | $^{13}$C (δ in ppm) | | | |
|---|---|---|---|---|
| Compound | C1, C2 | C3, C6 | C4, C5 | C1', C2' |
| en | — | — | — | 37.67 |
| cis-(1,2-DACH) | 58.2 | 35.26 | 26.36 | — |
| (1) | 61.74 | 26.13 | 20.64 | 50.39 |
| trans-(±)-(1,2-DACH) | 58.46 | 35.55 | 26.63 | — |
| (2) | 64.59 | 32.95 | 24.12 | 50.63 |
| (S,S)-(+)-(1,2-DACH) | 58.27 | 35.32 | 26.43 | — |
| (3) | 64.44 | 32.84 | 24.02 | 50.48 |

Example 6

Solid State NMR Studies

Solid-state $^{13}$C NMR spectra were recorded on a Bruker 400 MHz spectrometer at ambient temperature of 298 K. Samples were packed into 4 mm zirconium oxide (ZrO) rotors. Cross polarization (CP) and high power (HP) decoupling were employed. Pulse delay of 7.0 s and a contact time of 5.0 ms were used in the CPMAS experiments. The magic angle spinning (MAS) rates were maintained at 4 and 8 kHz. 13C chemical shifts were referenced to tetramethylsilane (TMS) by setting the high frequency isotropic peak of solid adamantane to 38.56 ppm. The solid-state NMR data are given in Table 7.

TABLE 7

Solid-state $^{13}$C NMR chemical shifts of free ligands and complexes 1, 2 and 3 in D$_2$O.

| | $^{13}$C (δ in ppm) | | | | |
|---|---|---|---|---|---|
| Complex | C1, C2 | C3, C6, | C4, C5 | C1', C2' | Refs. |
| [cis-(1,2-DACH)}AuCl$_2$]Cl | 66.20, 65.35 | 30,98 | 27.02, 22.12 | — | Hartinger and Dyson 2009 |
| (1) | 64.32 | 28.85 | 28.85, 22.94 | 54.3 | This work |
| [trans-(±)-(1,2-DACH)AuCl$_2$]Cl | 69.6 | 37.37 | 27.99 | — | Hartinger and Dyson (2009) |
| (2) | 69.60, 65.45 | 36.63 | 27.53 | 54.08 | This work |
| [(S,S)-(+)-(1,2-DACH)AuCl$_2$]Cl | 70.21 | 37.86 | 29.16 | — | Hartinger and Dyson (2009) |
| (3) | 67.1 | 36.19 | 27.65 | 54.18 | This work |

Example 7

Stability Determination of the Gold(III) Complexes

The stability of complexes 1, 2 and 3 were tested in water as well as in a mixture of solvents i.e. DMSO/water (2/1 in v/v ratio) by $^1$H and $^{13}$C NMR measurements. To investigate the structural stability of the complexes, NMR spectra of the complexes dissolved in D$_2$O; and in mixed DMSO-d$_6$/D$_2$O (2/1 in v/v ratio) solution were obtained just after dissolution, 24 h and 1 week at room temperature in mixed DMSO-d$_6$/D$_2$O and at 37° C. in D2O. At least 20 mg of complexes 1, 2 and 3 in 1 mL D$_2$O at 37° C.; and in 1 mL DMSO-d$_6$/D$_2$O (2/1:v/v) at room temperature were subjected to $^1$H and $^{13}$C NMR measurements and followed by their spectral analysis. Immediately after dissolution of complexes 1, 2 and 3 in the respective solvents and duplicate samples were then stored at room temperature and 37° C., respectively, and analyzed again after 24 h and 1 week in order to determine stability of complexes. Since the complexes were not used beyond a week after dissolution, so NMR measurements were limited to one week.

Example 8

Electrochemistry

The electrochemical experiments were performed at room temperature using a potentiostat (SP-300, Bio-Logic Science Instruments) controlled by EC-Lab v10.34 software package. The electrochemical experiments were performed at room temperature. All the measurements were performed on solutions de-aerated by bubbling ultra-pure nitrogen for 15 min. The values of reduction potential here reported were measured against a saturated calomel electrode (SCE). The cyclic voltammetry of the compounds 1, 2 and 3 were measured at scan rate of 50 mV/s on a reference buffer (40 mM phosphate, 4 mM NaCl, pH 7.4) using platinum as working electrode and graphite as a counter electrode with a concentration of 1.0 mM at room temperature. Ferrocene was used as pseudo reference to calibrate the working electrode. The couple FeIII/II formal potential of ferrocene occur at $E^{o\prime}=+0.44$ V(vs SCE) in 0.1 MBu$_4$NPF$_6$ solution in CH$_3$CN solvent which is similar to the report value under the same experimental condition [Hans J, Beckmann A, Kruger H-J (1999) Stabilization of Copper(III) ions with deprotonated hydroxyiminoamide ligands: syntheses, structures, and electronic properties of Copper(II) and Copper(III) complexes. Eur J Inorg Chem 1:163-172—incorporated herein by reference in its entirety]. Conversion to values vs ENH was obtained upon adding+0.24 V to the corresponding SCE values.

Example 9

Computational Studies

The structures of the [(1,2-DACH)Au(en)]$^{3+}$ complexes in their four possible conformations (cis-S,R or 1(a) as in Table 8; cis-R,S or 1(b); trans-S,S or 2(a), and trans-R,R or 2(b)) were studied without any geometrical constrains using GAUSSIAN09 program [Frisch M J, Trucks G W, Schlegel H B, Scuseria G E, Robb M A, Cheeseman J R, Scalmani G, Barone V, Mennucci B, Petersson G A, Nakatsuji H, Caricato M, Li X, Hratchian H P, Izmaylov A F, Bloino J, Zheng G, Sonnenberg J L, Hada M, Ehara M, Toyota K, Fukuda R, Hasegawa J, Ishida M, Nakajima T, Honda Y, Kitao O, Nakai H, Vreven T, Montgomery J A, Jr., Peralta J E, Ogliaro F, Bearpark M, Heyd J J, Brothers E, Kudin K N, Staroverov V N, Kobayashi R, Normand J, Raghavachari K, Rendell A, Burant J C, Iyengar S S, Tomasi J, Cossi M, Rega N, Millam J M, Klene M, Knox J E, Cross J B, Bakken V, Adamo C, Jaramillo J, Gomperts R, Stratmann R E, Yazyev O, Austin A J, Cammi R, Pomelli C, Ochterski J W, Martin R L, Morokuma K, Zakrzewski V G, Voth G A, Salvador P, Dannenberg J J, Dapprich S, Daniels A D, FarkasO", Foresman J B, Ortiz J V, Cioslowski J, and Fox D J (2009) Gaussian 09, Revision A.1, Gaussian, Inc., Wallingford Conn.—incorporated herein by reference in its entirety]. The hybrid B3LYP density functional (the three-parameter Becke functional with correlation from the Lee-Yang-Parr functional) with the Los Alamos National Laboratory-2 double-ζ (LANL2DZ) basis set was employed in this study [Becke A D (1988) Density-functional exchange-energy approximation with correct asymptotic behavior. Phys Rev 38:3098; Wadt W R, Hay P J (1985a) Ab initio effective core potentials for molecular calculations. Potentials for the transition metal atoms Sc to Hg. J Chem Phys 82:270-283; Wadt W R, Hay P J (1985b) Ab initio effective core potentials for molecular calculations. Potentials for main group element Na to Bi. J Chem Phys 82:284-298; Wadt W R, Hay P J (1985c) Ab initio effective core potentials for molecular calculations. Potentials for K to Au including the outermost core orbitals. J Chem Phys 82:299-305—each incorporated herein by reference in its entirety]. Previously reported results for some gold(III)-based complexes at this level of calculations are consistent with the experimental findings described herein [Al-Maythalony B A, Wazeer M I M, Isab A A (2009) Synthesis and characterization of gold(III) complexes with alkyldiamine ligands. Inorg Chim Acta 362:3109-3113—incorporated herein by reference in its entirety]. Moreover, the stationary points have been confirmed by frequency calculation. Selected bond lengths and bond angles are given in Table 8 for the four molecular conformations, while Table 9 compares the relative stabilities based on the calculated energies of these minimum structures.

TABLE 8

Selected bond lengths and bond angles of the [(1,2-DACH)Au(en)]$^{3+}$ complex in its four possible conformations.

|  | 1(a) | 1(b) | 2(a) | 2(b) |
|---|---|---|---|---|
| Bond lengths (Å) |  |  |  |  |
| Au—N$_1$ | 2.147 | 2.14 | 2.145 | 2.146 |
| Au—N$_2$ | 2.147 | 2.132 | 9.145 | 2.146 |
| Au—N$_3$ | 2.131 | 2.118 | 2.134 | 2.135 |
| Au—N$_4$ | 2.132 | 2.197 | 2.134 | 2.135 |
| N$_1$—C | 1.538 | 1.54 | 1.539 | 1.539 |
| N$_2$—C | 1.538 | 1.541 | 1.539 | 1.539 |
| N$_3$—C | 1.544 | 1.559 | 1.545 | 1.544 |
| N$_4$—C | 1.545 | 1.552 | 1.545 | 1.544 |
| Bond angles (°) |  |  |  |  |
| N$_1$—Au—N$_3$ | 177.7 | 179.5 | 179.4 | 179.5 |
| N$_2$—Au—N$_4$ | 177.6 | 179.4 | 179.4 | 179.5 |
| N$_1$—Au—N$_2$ | 81.8 | 82.1 | 82 | 81.9 |
| N$_2$—Au—N$_3$ | 100.5 | 98.3 | 98.6 | 98.6 |
| N$_3$—Au—N$_4$ | 77.2 | 81.7 | 80.9 | 80.9 |
| N$_4$—Au—N$_1$ | 100.6 | 97.9 | 98.5 | 98.6 |
| Au—N$_1$—C | 109.3 | 109.1 | 109 | 109 |
| Au—N$_2$—C | 109.1 | 109.1 | 109 | 109 |
| Au—N$_3$—C | 111.4 | 109.5 | 110.7 | 110.8 |
| Au—N$_4$—C | 111.8 | 109.4 | 110.7 | 110.8 |

TABLE 9

Relative energies of the four possible conformations of the complexes 1 and 2.

| Conformation | Relative energy (kcal/mol) |
|---|---|
| 1(a) | 3.61 |
| 1(b) | 3.1 |
| 2(a) | 0 |
| 2(b) | 0.11 |

Example 10

MTT Assay for Antiproliferative Effects of [(1,2-DACH)Au(en)]Cl$_3$ Compounds 1, 2 and 3 on PC3 and SGC7901 Cancer Cells An MTT assay was used to obtain the number of living cells in the sample. Human gastric cancer SGC7901 and prostate cancer PC3 cells were seeded on 96-well plates at a predetermined optimal cell density, i.e. ca. 6,000 cells/100 µL per well in 96-well plates, to ensure exponential growth in the duration of the assay. After 24 h pre-incubation, the growth medium was replaced with the experimental medium containing the appropriate drug, using one of gold(III) compounds 1, 2 and 3 or a control using water. Six duplicate wells were set up for each sample, and cells untreated with drug served as a control. In one set of culture plates, human gastric cancer SGC7901 and human prostate PC3 cells were treated with 10 µM compounds 1, 2 and 3 as the drug and the control (water) for 24, 48 and 72 h. In other sets, the compounds 1, 2 and 3 with different concentration, i.e. 10, 20 and 30 µM, were employed to determine the growth inhibitory effect for both PC3 and SGC7901 cells separately. After incubation, 10 µL MTT (6 g/L, Sigma) was added to each well and the incubation was continued for 4 h at 37° C. After removal of the medium, MTT stabilization solution [dimethylsulfoxide (DMSO):ethanol (C$_2$H$_5$OH)=1:1 in v/v ratio] was added to each well, and shaken for 10 min until all crystals were dissolved. Then, the optical density was detected in a micro plate reader at 550 nm wavelength using an Enzyme-Linked Immuno-Sorbent Assay (ELISA) reader. After being treated with gold(III) complexes 1, 2 and 3, the cell viability was examined by MTT assay. Each assay was performed in triplicate. An MTT assay for the inhibitory effect has been used for compounds 1, 2 and 3 against PC3 and SGC7901 cells. These cells were treated with various concentrations of compounds 1, 2 and 3 for 24-72 h. All results are shown in FIGS. 1-7A and B.

Example 11

In Vitro Cytotoxic Assay for PC3 and SGC7901 Cancer Cells

Human prostate PC3 and gastric SGC7901 cells were used throughout the examples of the present disclosure. Cells were cultured in Dulbecco's Modified Eagle Medium (DMEM) supplemented with 10% fetal calf serum (FCS), penicillin (100 kU U$^1$) and streptomycin (0.1 g L$^{-1}$) at 37° C. in a 5% CO2-95% air atmosphere. Human gastric SGC7901 cells and prostate PC3 were incubated with these compounds at fixed concentrations or with water as a control to assess the inhibitory effect on cell growth. The standard MTT assay has been used to assess the inhibitory effect on cell growth. The cell survival versus drug concentration is plotted. Cytotoxicity was evaluated in vitro with reference to the IC$_{50}$ value. The half maximal inhibitory concentration (IC$_{50}$) is a measure of the effectiveness of a compound to inhibit biological or biochemical functions. According to the FDA, IC$_{50}$ represents the concentration of a drug/compound/complex that is required for 50% inhibition in vitro. It is evaluated from the survival curves as the concentration needed for a 50% reduction of survival. IC$_{50}$ values are expressed in µM. The IC$_{50}$ values were calculated from dose—response curves obtained in replicate experiments. The IC$_{50}$ data are presented in Table 10.

TABLE 10

In vitro cytotoxicity data of the complexes 1, 2 and 3 after exposure of 72 h towards human cancer SGC1901 and PC3 cell lines.

| Complex | IC$_{50}$ (µM)$^a$ | |
| --- | --- | --- |
| | SGC7901 | PC3 |
| Cisplatin | 7.3 ± 0.5 | 1.1 ± 0.1 |
| (1) | 5.5 ± 0.2 | 4.8 ± 0.1 |
| (2) | 7.9 ± 0.2 | 8.9 ± 0.1 |
| (3) | 5.8 ± 0.2 | 6.1 ± 0.1 |

Example 12

UV-Vis Spectra

The λ$_{max}$ values obtained from UV-Vis spectra for the complexes studied are shown in Table 2. The gold(III) compounds 1, 2 and 3 exhibit, in a reference buffered phosphate solution, intense absorptions in the range 335-339 nm, which are assigned as ligand-to-metal charge-transfer (LMCT) transitions characteristically associated to the gold (III) center. These absorption bands were previously assigned to NH$^-$—Au(III) charge-transfer bands [Kimura E, Kurogi Y, Takahashi T (1991) The first gold(III) macrocyclic polyamine complexes and application to selective gold(III) uptake. Inorg Chem 30:4117-4121—incorporated herein by reference in its entirety]. It is worth-mentioning that these spectral features appear only at relatively high pH values (pH>6-7) at which the deprotonation of ligand has fully occurred. According to crystal field theory for d$^8$ complexes the lowest unoccupied molecular orbital (LUMO) orbital is d$_{x2-y2}$, so ligand to metal charge transfer could be due to p$_o$→d$_{x2-y2}$ transition [Haruko I, Junnosuke F, Kazuo S (1967) Absorption spectra and circular dichroisms of metal complexes. I. Platinum(II)-, palladium(II)- and gold(III)-complexes containing optically active diamines. Bull Chem Soc Jpn 40:2584-2591—incorporated herein by reference in its entirety].

Figure 8A:
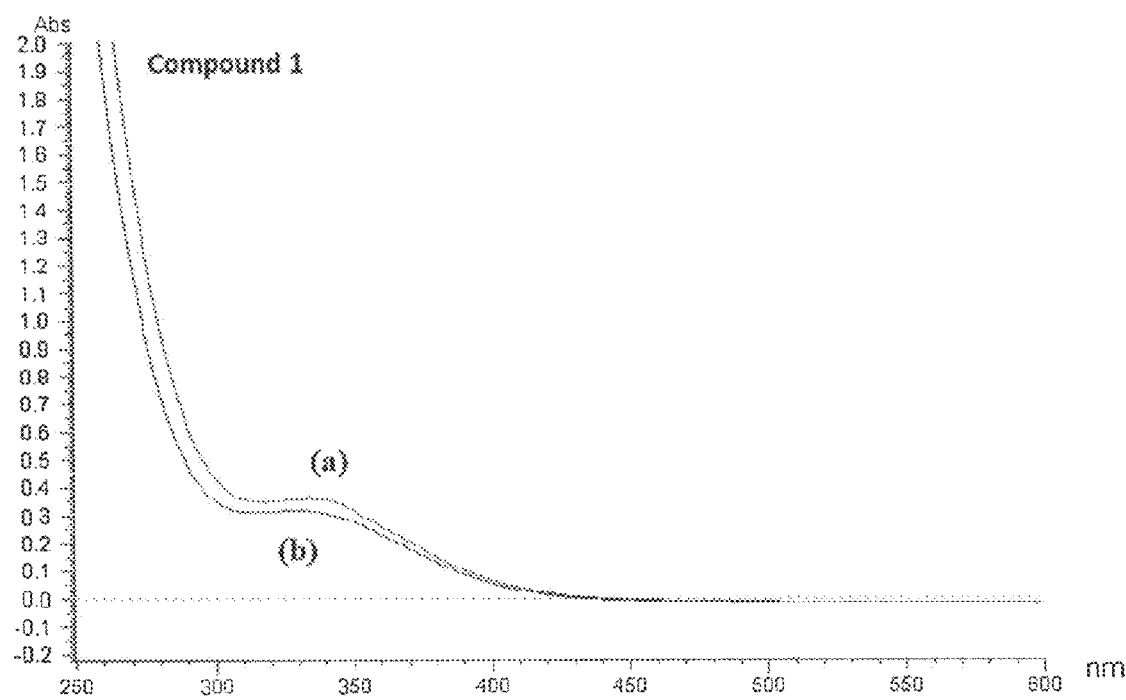
FIGS. 8A, 8B and 8C show UV-Vis spectra of Compounds 1, 2 and 3, respectively, followed by dissolution in the buffer solution at 37° C. (a) just after mixing and (b) after 7 days.
Figure 8B:
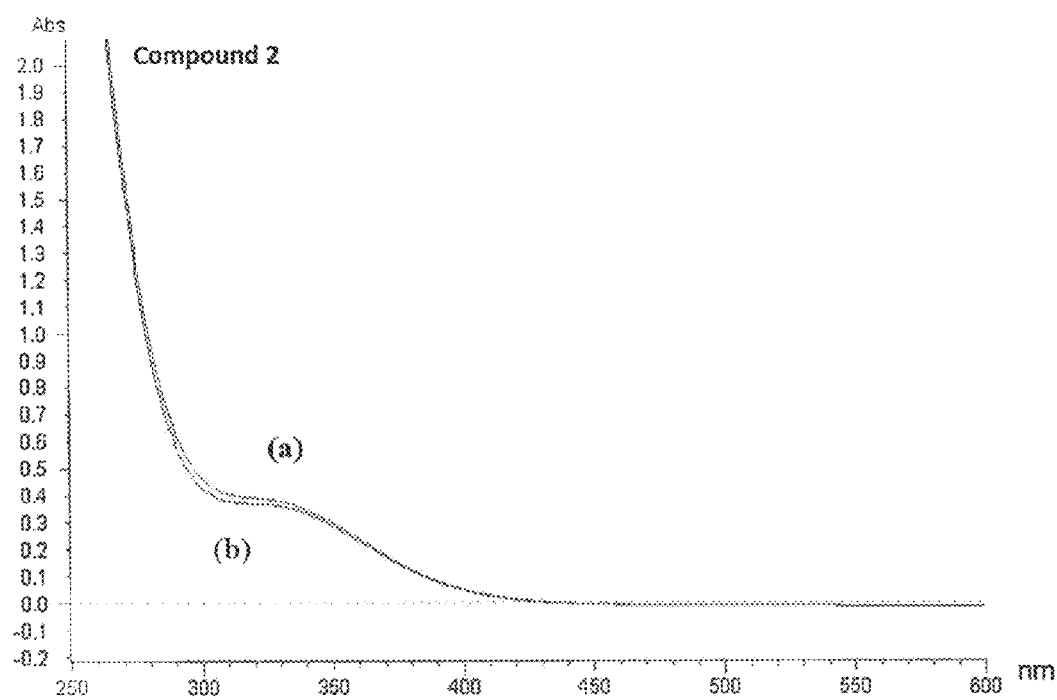
Figure 8C:
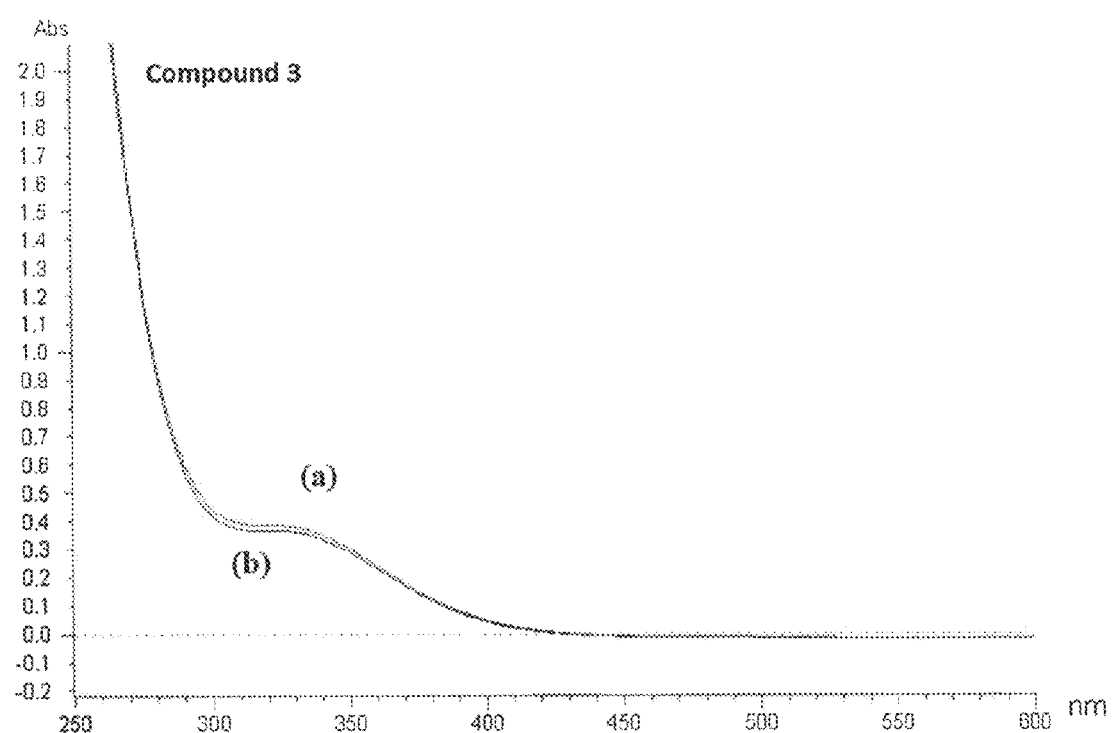

The electronic spectra of compounds 1, 2 and 3 were monitored at 37° C. over 3 days after mixing in the buffer solution. The electronic spectra for compounds 1, 2 and 3 at just after mixing; and after 3 days are illustrated in FIGS. 8A-8C. It is apparently observed that the transitions remain relatively unmodified over a period of 3 days. Such observations show a substantial evidence for the stability of these compounds 1, 2 and 3 under the conditions of solution state. Nevertheless, a slight decrease in intensity of the characteristic bands was noticed with time without significant modifications in shape of spectra. Further, such observation indicates that the gold center in these compounds remains in the +3 oxidation state. The minor spectral changes that are generally observed within the first hours may be ascribed either to dissociation of the amine ligands from the gold(III) complex or to partial reduction of gold(III) to metallic gold. In general, however, loss of spectral intensity is lower than 10% of the original intensity within the observation period of 7 days which indicates high stability of these compounds in the buffer. It is a possible proposition that compounds 1, 2 and 3 would be stable enough in the physiological environment to undergo the necessary reactions/interactions required for bioactivity, without decomposition.

Example 13

Mid- and Far-FTIR Spectroscopic Characterization

The most significant bands recorded in the FTIR spectra of the ligand, [(1,2-DACH)Au(en)]Cl$_3$ complexes have been reported in Tables 3 and 4. It is noted that N—H stretching vibrations of complexes 1, 2 and 3 exhibit, in the range 3,386-3,432 cm-1, blue shifting compared with the amino group of the corresponding free ligands. This is most likely due to stronger H-bonding interactions in the free ligands as compared to two coordinated amino-:NH2 groups of 1,2-diaminocyclohexane (1,2-DACH) via donor N atoms, leading to formation of five member chelate with gold(III) center in corresponding compounds 1, 2 and 3. The coordination of amino-:NH2 with Au(III) center via nitrogen donor atom and formation of Au—N bond can be supported by the presence of a m(Au—N) band at 417-442 cm-1 in the Far-FTIR [Beck W, Fehlhammer W P, Pollmann P, Schuierer E, Feldl K (1967) Darstellung, IR- und Elektronenspektren von Azido-Metall-Komplexen. Chem Ber 100:2335-2361—incorporated herein by reference in its entirety]. The C—N stretching bands also showed a significant shift to higher wave number, indicating a shorter C—N bond in the compound than in the free ligand. Moreover, there was no signal observed at 352 and 367 cm-1 corresponding to the symmetric and asymmetric stretching of the Cl—Au—Cl bonds in [(1,2-DACH)AuCl$_2$]$^+$ type compounds, indicating the absence of the mono-(1,2-DACH)gold(III) chloride compound [Al-Maythalony B A, Wazeer M I M, Isab A A (2009) Synthesis and characterization of gold(III) complexes with alkyldiamine ligands. Inorg Chim Acta 362:3109-3113—incorporated herein by reference in its entirety]. The [(1,2-DACH)Au(en)]Cl$_3$ complexes 1, 2 and 3 show N—H stretching frequencies generally lower in comparison with [(1,2-DACH)AuCl$_2$]Cl complexes (Table 3), most probably due to stronger hydrogen bonding interactions with the chloride anions in the [(DACH)Au(en)]Cl$_3$ complexes. Furthermore the Au—N stretching frequencies are consistent with weaker Au—N bond strength in complexes 1, 2 and 3 compared to [(1,2-DACH)AuCl$_2$]Cl complexes.

Example 14

Solution-State NMR Characterization

Figure 9:
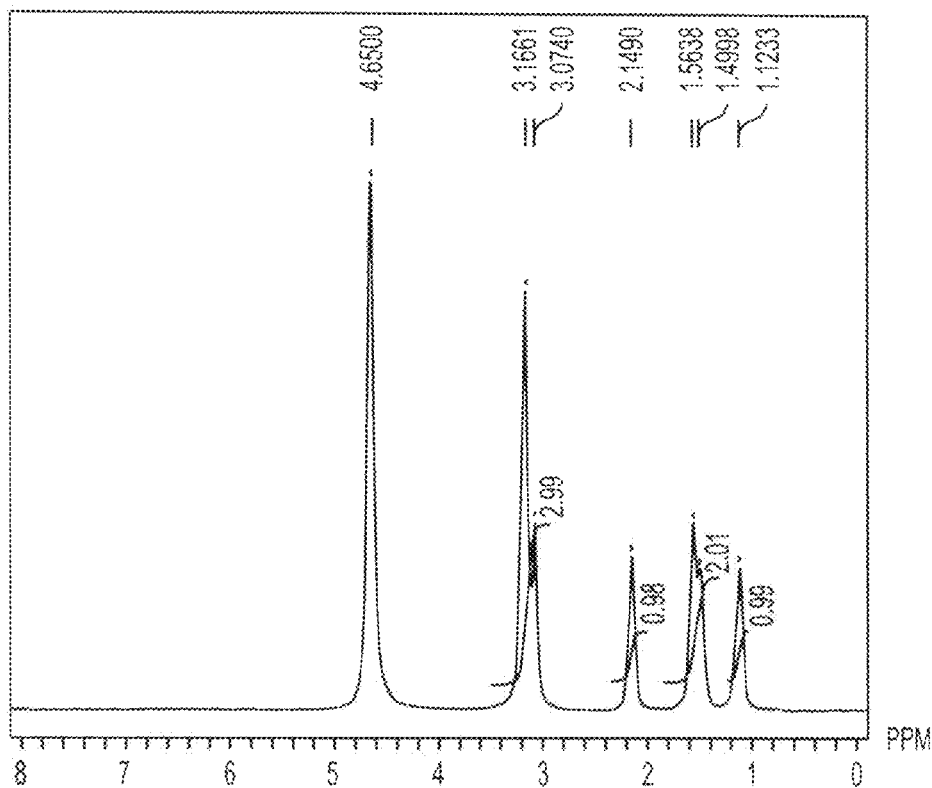
FIG. 9 is a solution state $^1$H NMR spectrum of [{(S,S)-(+)-(1,2-DACH)}Au(en)]Cl$_3$ complex.
Figure 10:
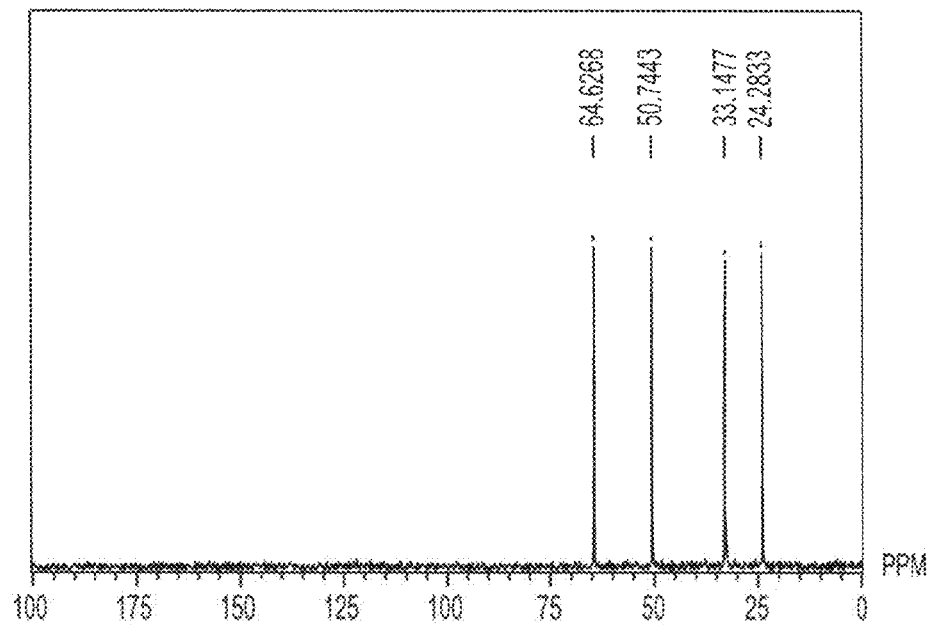
FIG. 10 is a solution state $^{13}$C{$^1$H} NMR spectrum of [{(S,S)-(+)-(1,2-DACH)}Au(en)]Cl$_3$ complex.
Figure 11A:
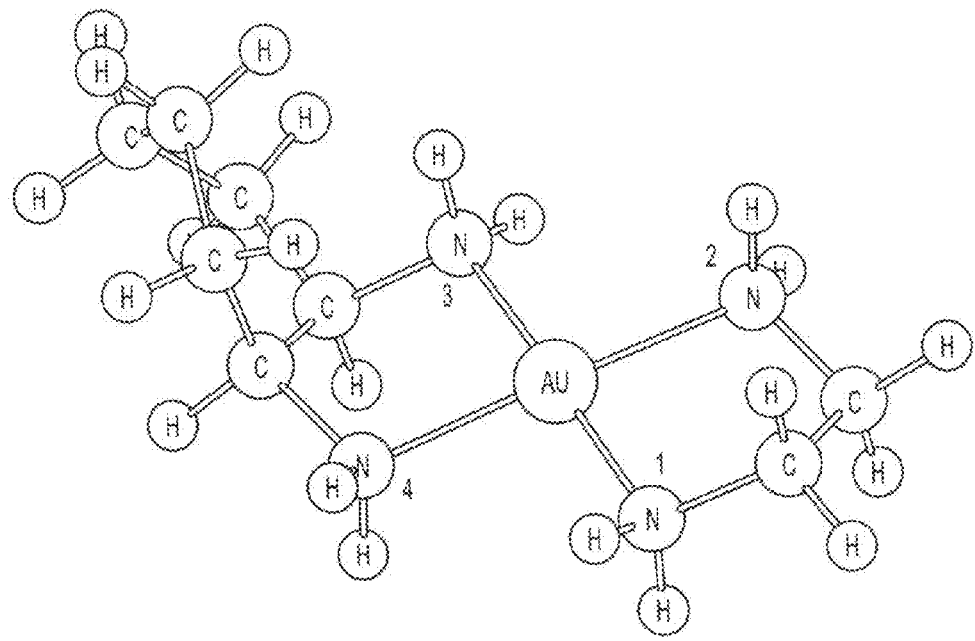
FIGS. 11A, 11B, 11C and 11D are geometries of 1(a), 1(b), 2(a) and 2(b), respectively, obtained at the B3LYP/LanL2DZ level of theory using GAUSSIAN09.
Figure 11B:
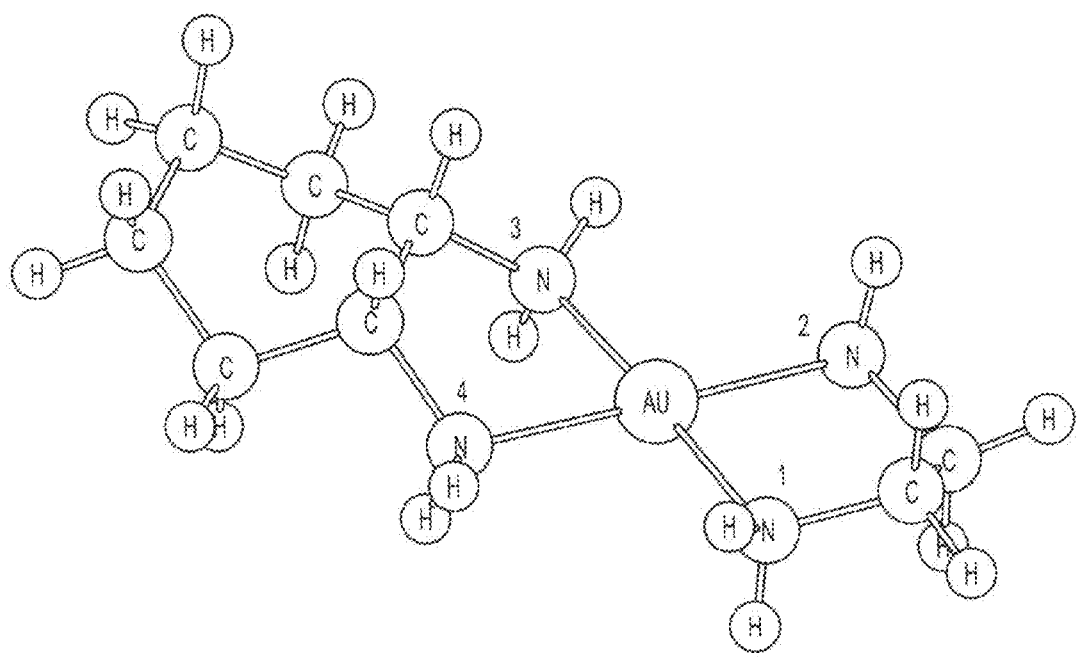
Figure 11C:
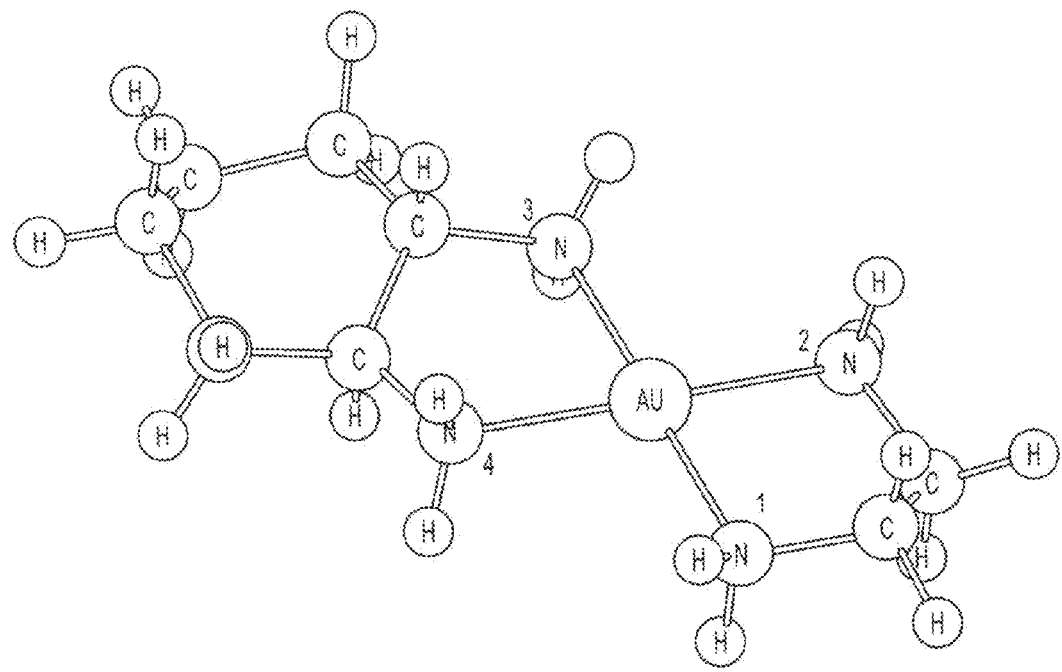
Figure 11D:
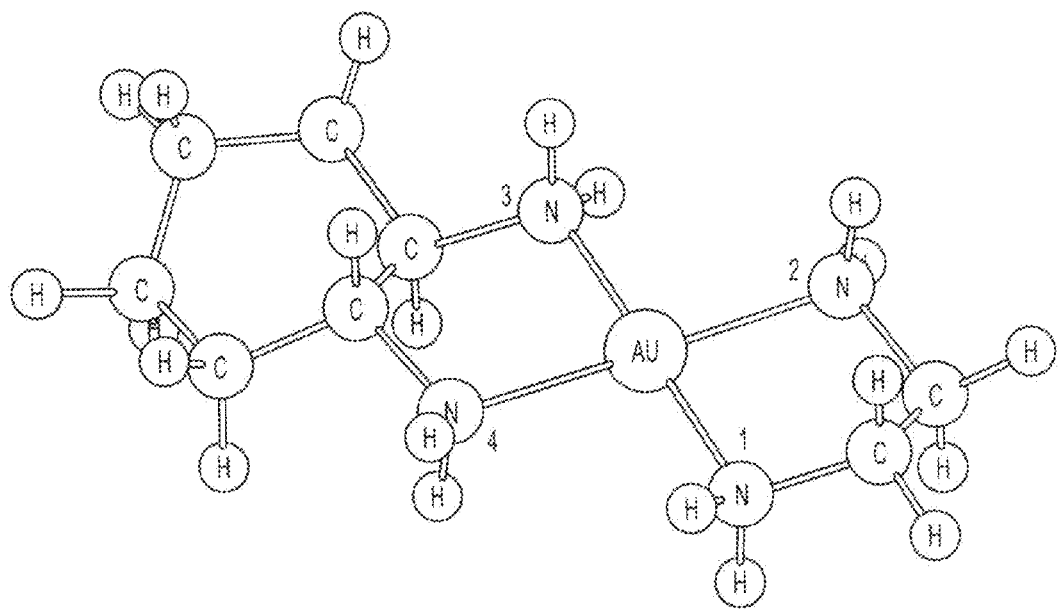

All $^1$H NMR spectra supported the structures of the synthesized complexes as indicated by the integration of the signals of C—H protons connected to the amino groups of the (1,2-DACH) and (en). For example, the ratio of the protons attached to amino group in both (1,2-DACH) and (en) for complex 3 is 1:2 as illustrated in FIG. 9. Its $^{13}$C NMR spectrum is also confirmed the complex structure as shown in FIG. 10. The $^1$H and $^{13}$C NMR chemical shifts of compounds 1-3 along with their corresponding free ligands are listed in Tables 5 and 6, respectively. In the $^1$H and $^{13}$C NMR spectra of complexes 1, 2 and 3, one half of the total number of signals were noticed because of the C$_2$ symmetry of the 1,2-diaminocyclohexane ring, which is considered as a rigid conformer that allowed, for instance, to distinguish equatorial H3 and H6 from axial H3 and H6 at room temperature. The signals of C—H protons connected to the amino groups for both (1,2-DACH) and (en) occur at 3.05-3.61 ppm, shifting downfield compared with the corresponding signals at 2.23-2.65 ppm in the free diamine ligands. The significant downfield shift was observed at 3.62 ppm for complex 1 with respect to the free cis-1,2-DACH ligand at 2.23 ppm. This can be attributed to the donation of nitrogen lone pairs to the gold center that causes de-shielding of the proton(s) next to the bonding nitrogen. On the other hand, $^{13}$C NMR downfield shift was observed only for the carbon next to the bonding nitrogen and the others carbons in the complex for (1,2-DACH) showed upfield shift presumably due to γ-shielding effect. For instance, chemical shift of C3 and C4 for complex 1 observed at 26.13 and 20.64 ppm, respectively, whereas, for free diamine ligand it occurs at 35.26 and 26.36 ppm. It is also worth-mentioning that complexes 1-3, even though they have the same skeleton of (1,2-DACH) and (en), their carbon chemical shifts were not the same due to a different stereochemistry upon coordination.

Example 15

Solid-State NMR Characterization

As listed in Table 7, solid state NMR spectrum of complex 3 showed equivalency in the chemical shifts of carbon atoms (C1, C2), (C3, C6), (C4, C6) and (C1, C2) where two sets of peaks were observed, whereas, a similar behavior was not observed for carbon atoms of (DACH) in complexes 1 and 3. This indicates that these complexes 1 and 3 in the solid state lack C$_2$ symmetry, due to packing effect. In contrast, all synthesized complexes 1, 2 and 3 showed C$_2$ symmetry in the solution state as indicated earlier by solution $^1$H and $^{13}$C NMR.

Compared to solution chemical shifts, significant de-shielding in solid state is observed with similarity in chemical shift trends among all complexes 1-3 as given in Table 7, which is a clear indication of stability of the structural similarity in solid state as well as in solution state.

Example 16

Computational Analysis

The structures of the [(1,2-DACH) Au(en)]$^{3+}$ complexes as obtained from the B3LYP/LANL2DZ level of calculations are shown in FIGS. 11A-D. Selected quantitative structural parameters are also listed in Table 8. The complexes show a distorted square planar geometry structure around the gold(III) center. The N—Au—N angles in most of the conformations are within less than a degree from the perfect square planar geometry. The Au—N was predicted to be in the range of 2.12-2.15 Å for both (1,2-DACH) and (en) bidentate diamine ligands. The C—N bond length shows a significant increase by ca. 0.1 Å when it is compared with the same type of bonds in normal amines [Allen F H, Kennard O, Watson D G, Brammer L, Orpen A G (1987) Tables of bond lengths determined by X-ray and neutron diffraction. Part 1. bond lengths in organic compounds. J Chem Soc Perkin Trans II:S1-S19—incorporated herein by reference in its entirety].

The four coordinated nitrogen atoms (two N from 1,2-DACH and two N from en) are predicted to adopt a sp$^3$ type of hybridization as it can easily be concluded by viewing the calculated bond angles (Table 8). From the computed energetics of the four structures of the complexes 1 and 2 (Table 9), the trans-conformations are more preferable compared to the cis-conformations with more than 3.5 kcal/mol difference. The most possible explanation of this energy variation is the ring configuration of the 1,2-DACH ligand, where the methylene (CH$_2$) units experience more steric repulsion in the cis form in comparison to that in the trans form.

Example 16

Stability Determination of Mixed Diamine Ligand Gold(III) Compounds

Figure 15A:
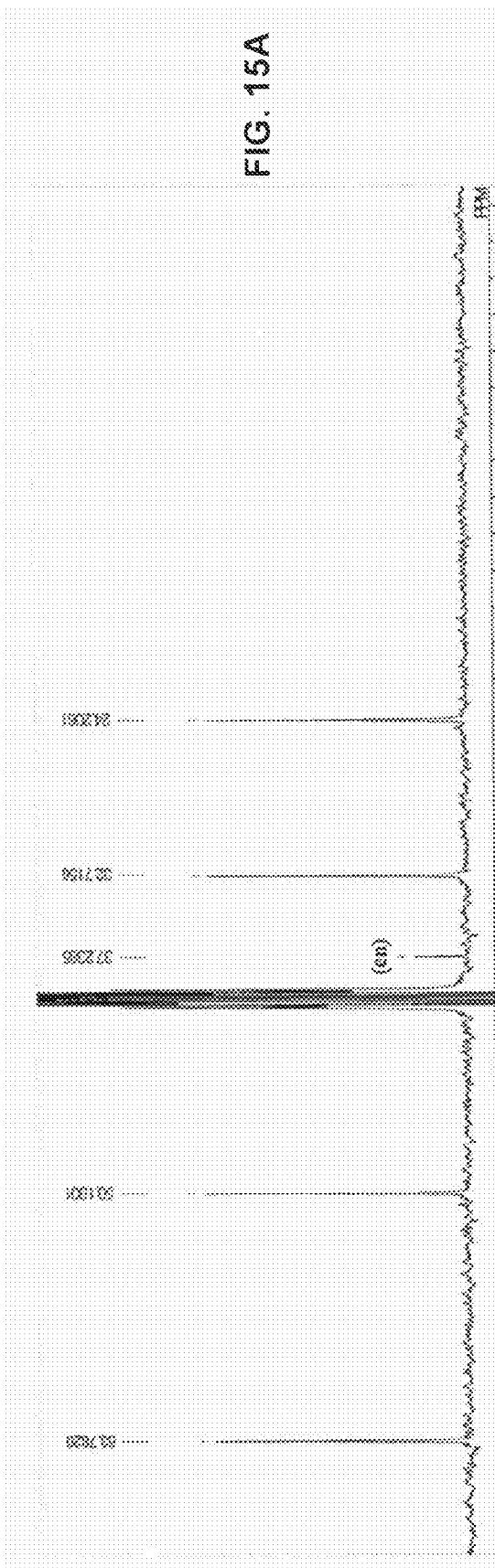
FIGS. 15A and 15B are solution state $^{13}C\{^1H\}$ NMR spectra of [{(S,S)-(+)-(1,2-DACH)}Au(en)]Cl$_3$ complex in D$_2$O at after 7 days and just after mixing, respectively.
Figure 15B:
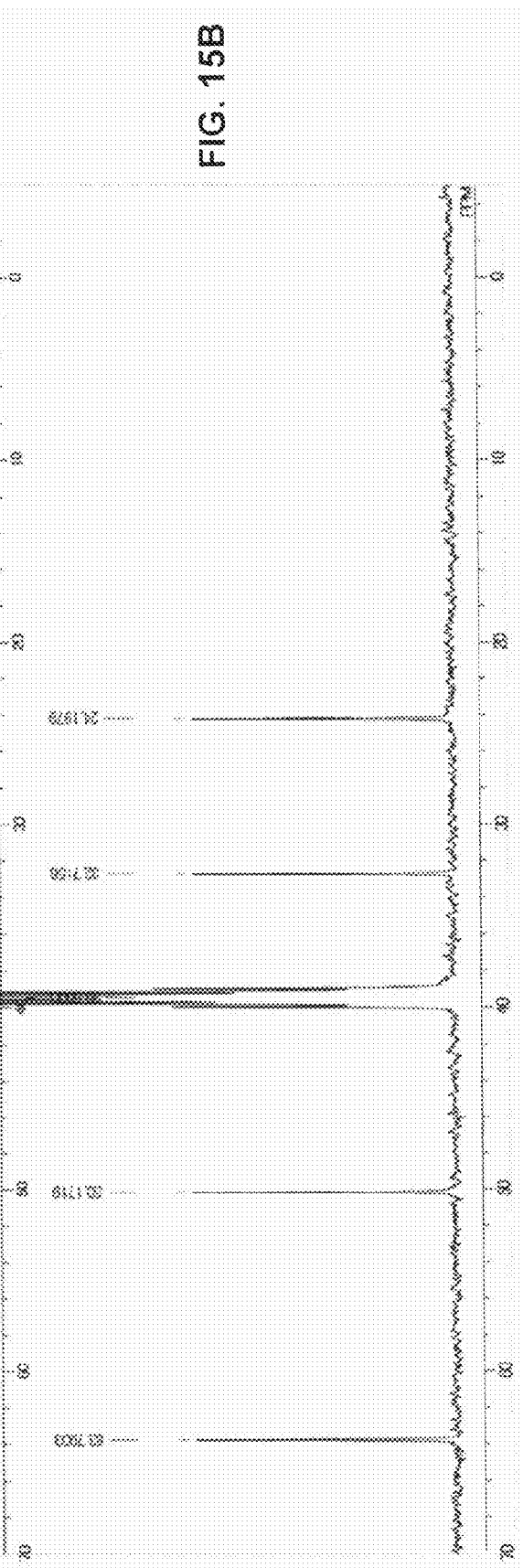

NMR spectra of the complexes were obtained upon immediate dissolution to serve as reference spectra and later at 24 h and after 7 days at 37° C. in D$_2$O and at room temperature in mixed DMSO-d$_6$/D$_2$O in order to determine their stability. In general, all complexes showed high stability in D$_2$O as well as in mixed DMSO-d$_6$/D$_2$O and their NMR profiles remained unchanged over the span of 7 days. For example, FIGS. 12A-B and 13A-B illustrated, respectively, the $^1$H and $^{13}$C NMR profiles of the compound 1 at just after mixing and after 7 days. Whereas, these compounds in mixed DMSO-d$_6$/D$_2$O solvent system were slightly less stable at the experimental conditions, in which, minor dissociation of ethylenediamine (en) out of the gold complexes was observed in 24 h. On the other hand, no dissociation was observed for (1,2-DACH). Among all synthesized complexes, the maximum dissociation for ethylenediamine (en) after 7 days was experienced for compound 3 with 25%. $^1$H and $^{13}$C NMR profiles of compound 3 in DMSO-d$_6$/D$_2$O at just after mixing and after 7 days as shown in FIGS. 14A-B and 15A-B respectively. $^1$H and $^{13}$C NMR of compound 3 spectra after 7 days in DMSO-d6/D2O showed extra peak at 3.07 and 37.24 ppm as shown in FIGS. 14B and 15B, respectively, corresponding to the free (en) atoms. It is concluded that the bond between gold(III) and (1,2-DACH) is stronger than the bond between gold(III) and (en) in these complexes 1-3, suggesting that ethylenediamine (en) could be a better leaving group.

Example 17

Electrochemical Behavior of Mixed Diamine Ligand Gold(III) Complexes

Figure 16A:
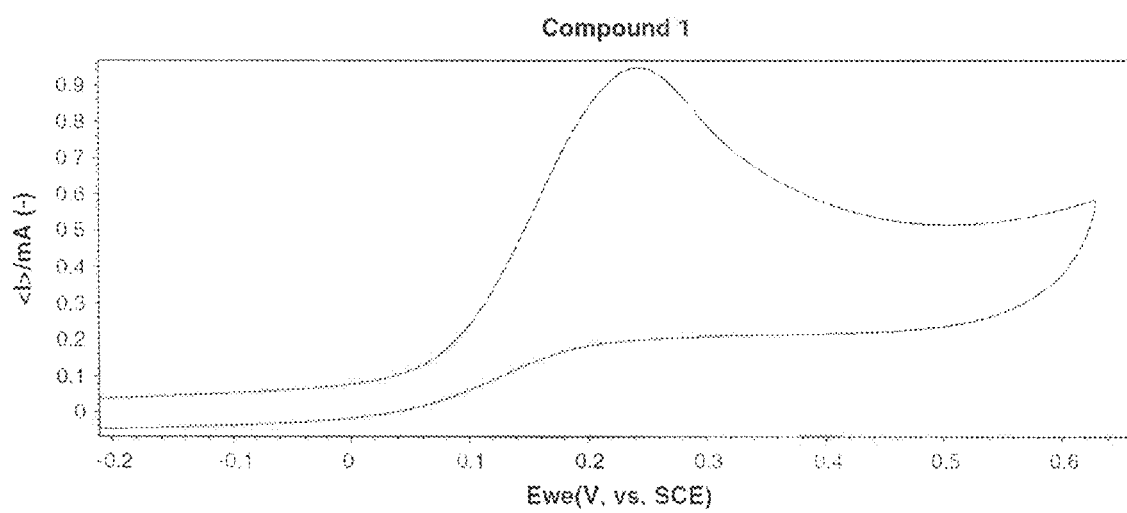
FIGS. 16A, 16B and 16C are cyclic voltammograms of Compounds 1, 2 and 3, respectively, in the phosphate buffer at platinum electrode.
Figure 16B:
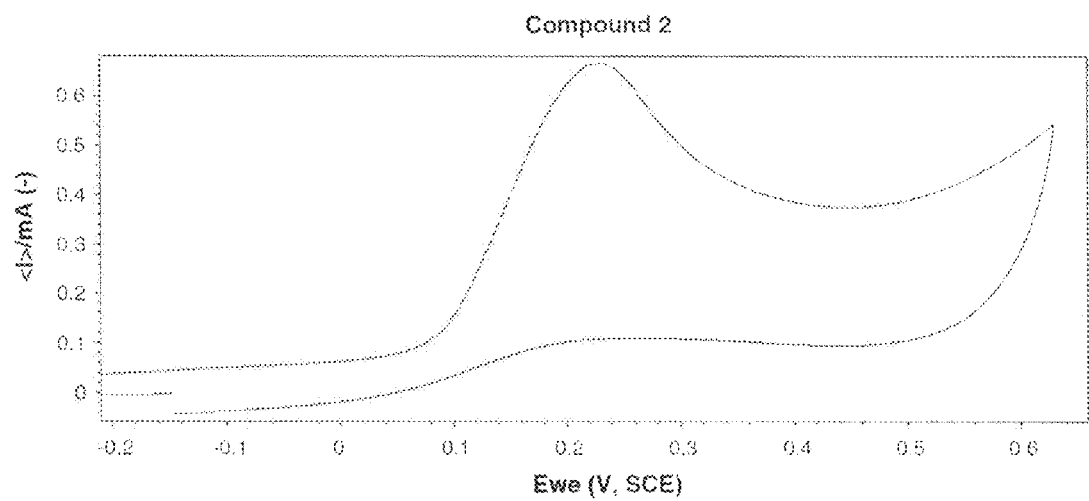
Figure 16C:
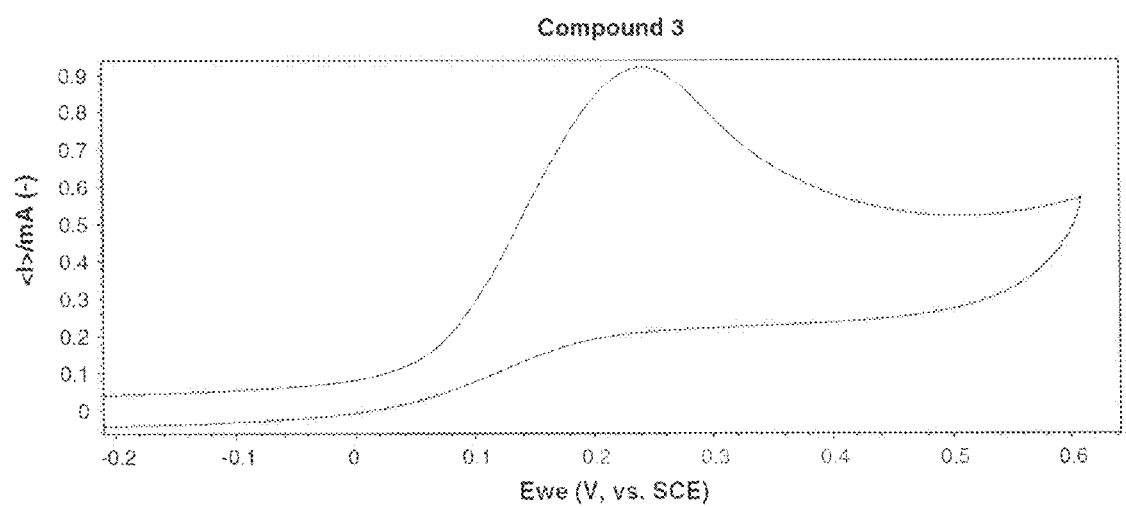

The electrochemical behavior of compounds (1, 2 and 3 was investigated in a physiological environment through cyclic voltammetry (CV). The cyclic voltammetric curves of the complexes 1, 2 and 3 are shown in FIGS. 16A-C. Table 11 summarizes the cyclic voltammetric data of all the studied compounds. The reduction potential values vs. NHE for the reduction processes exhibited by the complexes 1, 2 and 3, in a reference phosphate buffer solution, were in the range (+0.46)-(+0.51) V. Cyclic voltammetric data indicated that trans-1,2-DACH conformer is slightly more stable than the cis-1,2-DACH conformer of the complexes which is also corroborated by UV-Visible spectral studies. Gold(III) complexes 1, 2 and 3 show one irreversible reduction process in which the controlled potential coulometry involves three electrons per mole. The occurrence of Au(III)/Au(0) reduction is visually indicated by the appearance of a thin gold layer deposited on the platinum electrode surface after exhaustive electrolysis (Ew, −0.7 V). In general, cyclic voltammetric results suggest that these compounds are quite stable under the physiological conditions.

The stability of the gold(III) compounds in the reference phosphate buffer was also checked after the addition of stoichiometric amounts of the biologically important reducing agent sodium ascorbate. It was observed that all complexes were quickly and almost completely reduced in 60 min.

TABLE 11

Peak potential values vs. ENH for reduction of gold(III) complexes.

| Complex | $E_p$ (V) |
|---|---|
| (1) | 0.49 |
| (2) | 0.46 |
| (3) | 0.51 |

Example 18

Antiproliferative Effects of Gold(III) Complexes 1, 2 and 3 on Prostate (PC3) and Gastric (SGC7901) Cancer Cells Modern oncologic or anticancer studies aim towards designing newer compounds showing enhanced antiproliferative potential and not as much of associated toxicity than cisplatin. In this connection, gold(III) complexes with various ligands including Au—N, Au—S or Au—C bonds are being extensively developed and investigated for their bioactivities as antiproliferative agents [Ott I, Gust R (2007) Non platinum metal complexes as anticancer drugs. Arch Pharm Chem Life Sci 340:117-126; Ahmed A, Al Tamimi D M, Isab A A, Alkhawajah A M M, Shawarby M A (2012) Histological changes in kidney and liver of rats due to gold(III) compound [Au(en)Cl$_2$]Cl. PLoS ONE 7:e51889—each incorporated herein by reference in its entirety]. In the present disclosure, a new series of gold(III) complexes 1-3 containing mixed ethylenediamine (en) and 1,2-DACH ligands are being evaluated for antiproliferation against PC3 and SGC7901 cancer cell lines.

FIGS. 1-3A and B illustrated time dependent antiproliferative effects of complexes 1, 2 and 3 respectively. In the time dependent, the growth inhibition on PC3 and SGC7901 cancer cells was studied using fixed concentration i.e. 10 µM. It can be seen from these figures that time-dependent antiproliferative effects of complexes 1, 2 and 3 on PC3 cancer cells are better than those on SGC7901 cancer cells. Complexes 1 and 3 showed better cell inhibition against PC3 cell line than complex 2 as shown in these figures. However, Complex 1 showed better cell inhibition against SGC7901 cancer cell line than complexes 2 and 3 as shown in FIGS. 1-3A and B. Gold(III) complexes 1 and 3 demonstrated a comparable cell inhibition; against PC3 cell line as shown in FIGS. 1A and B, 3A and B, whether the complexes exposure time was 24 or 72 h. All the gold(III) complexes showed lower cell inhibition against both cancer cell lines for 72 h exposure time compared to 24 h as shown in FIGS. 1-3A and B.

Figure 4A:
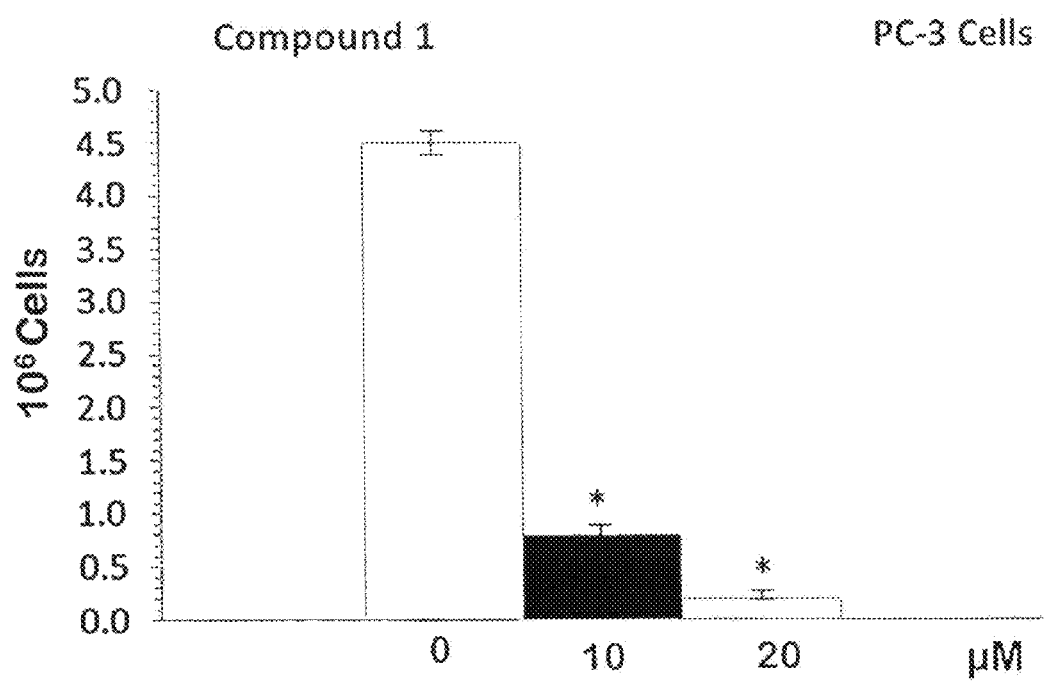
FIGS. 4A and 4B are bar graphs showing the concentration-dependent antiproliferative effect of 10 μM Compound 1 on PC3 and SGC7901 cells, respectively, for 24 and 72 h using MTT assay where results were expressed as the mean, SD, *P<0.05.
Figure 4B:
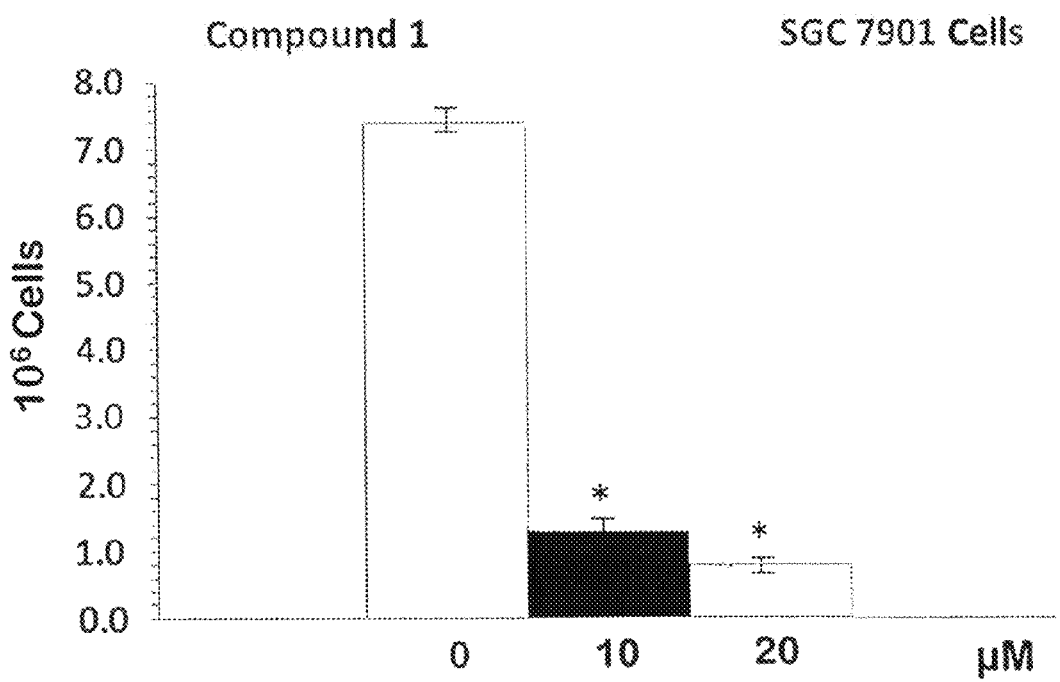
Figure 5A:
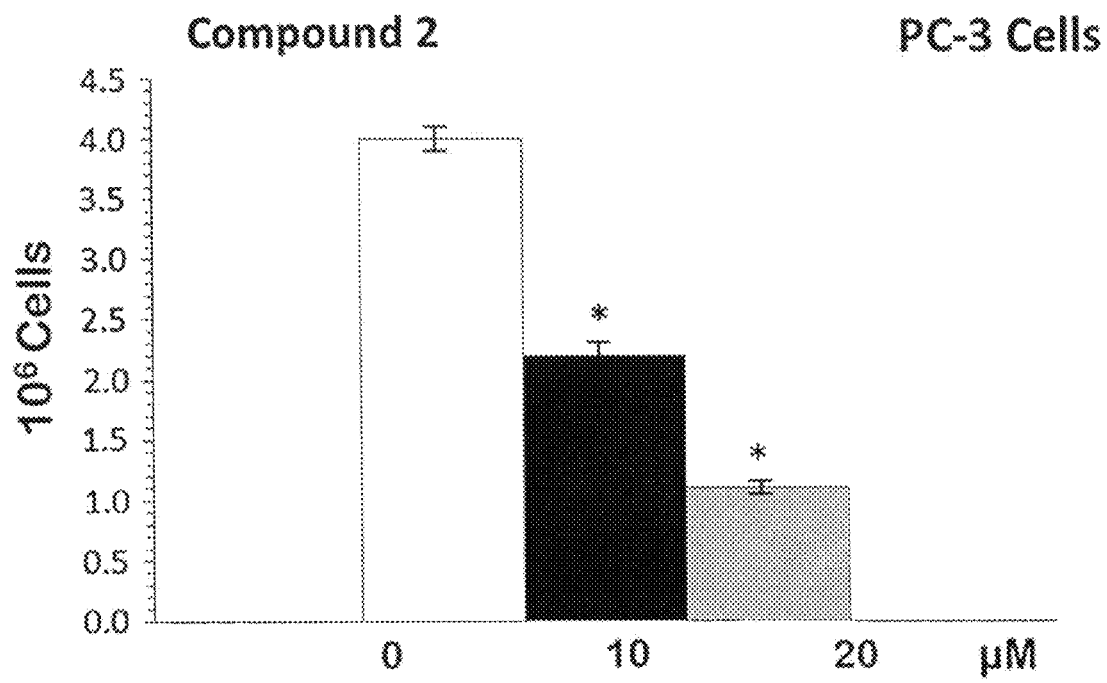
FIGS. 5A and 5B are bar graphs showing the concentration-dependent antiproliferative effect of 10 μM Compound 2 on PC3 and SGC7901 cells, respectively, for 24 and 72 h using MTT assay where results were expressed as the mean, SD, *P<0.05.
Figure 5B:
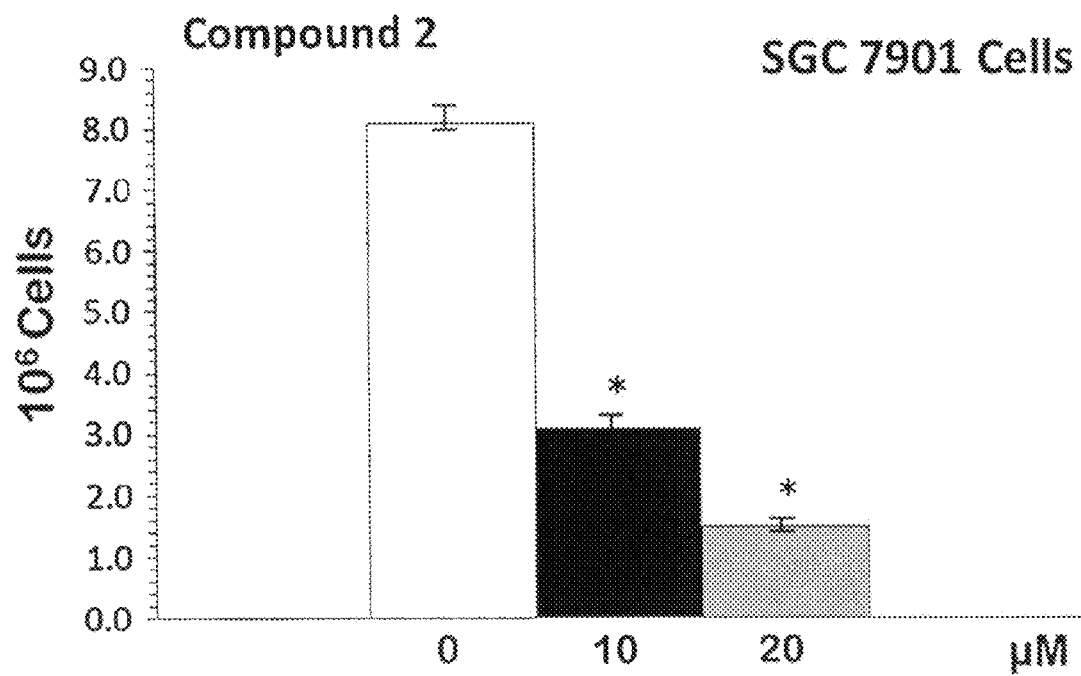
Figure 6A:
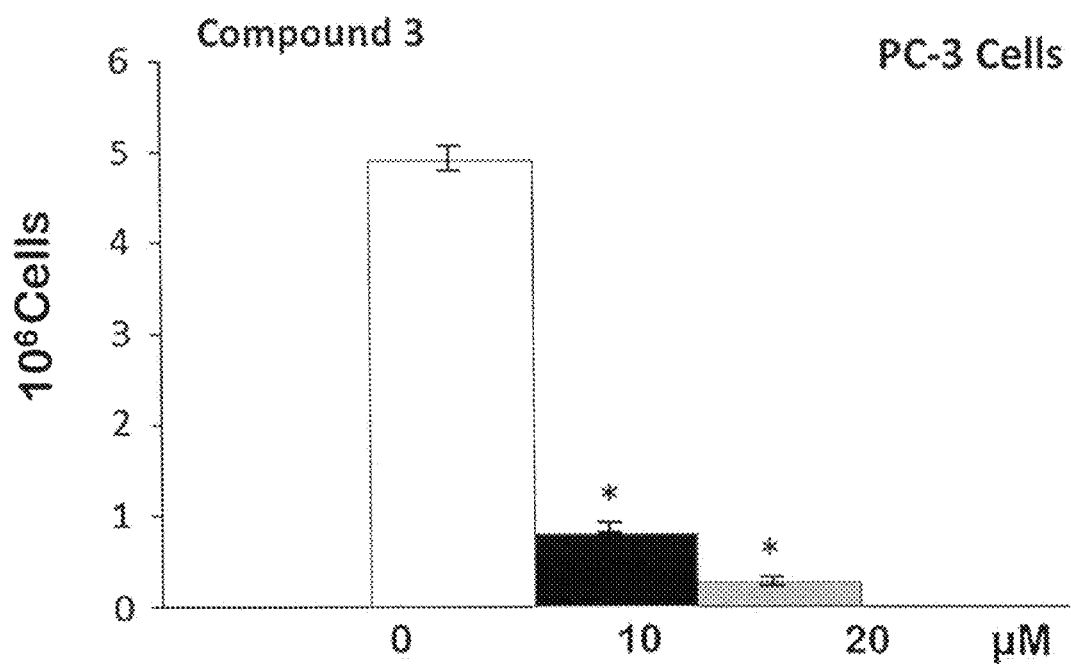
FIGS. 6A and 6B are bar graphs showing the concentration-dependent antiproliferative effect of 310 μM Compound 3 on PC3 and SGC7901 cells, respectively, for 24 and 72 h using MTT assay where results were expressed as the mean, SD, *P<0.05.
Figure 6B:
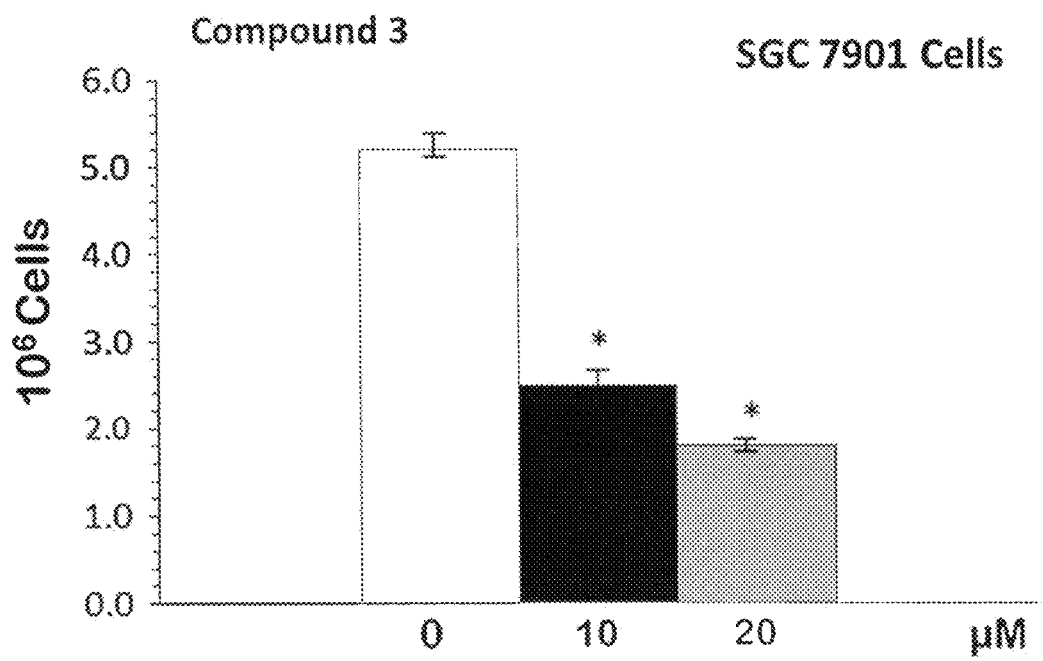

Cell growth inhibition is also dependent on concentration of the drug. So, concentration-dependent cell growth inhibition studies of gold(III) complexes 1-3 against human prostate PC3 and gastric SGC7901 cancer cells were conducted by using 10 and 20 µM concentrations. The results included cell inhibition augmented with the increase in concentration of the complexes 1, 2 and 3 as shown in FIGS. 4-6A and B, respectively. It is generally observed from these figures that concentration-dependent antiproliferative effects of complexes 1, 2 and 3 on PC3 cancer cells are superior to those on SGC7901 cancer cells. In the concentration-dependent cell growth inhibition study at two concentrations (10 and 20 µM), complex 1 showed better cell inhibition against SGC7901 cancer cell line than complexes 2 and 3 as shown in FIGS. 4-6A and B; whereas complexes 1 and 3 showed better cell inhibition against PC3 cell line than complex 2, as shown in the figures. Gold(III) complexes 1 and 3 demonstrated a comparable cell inhibition; against PC3 cell line at 20 µM concentration as shown in FIGS. 4A and B and 6A and B, respectively.

Figure 7A:
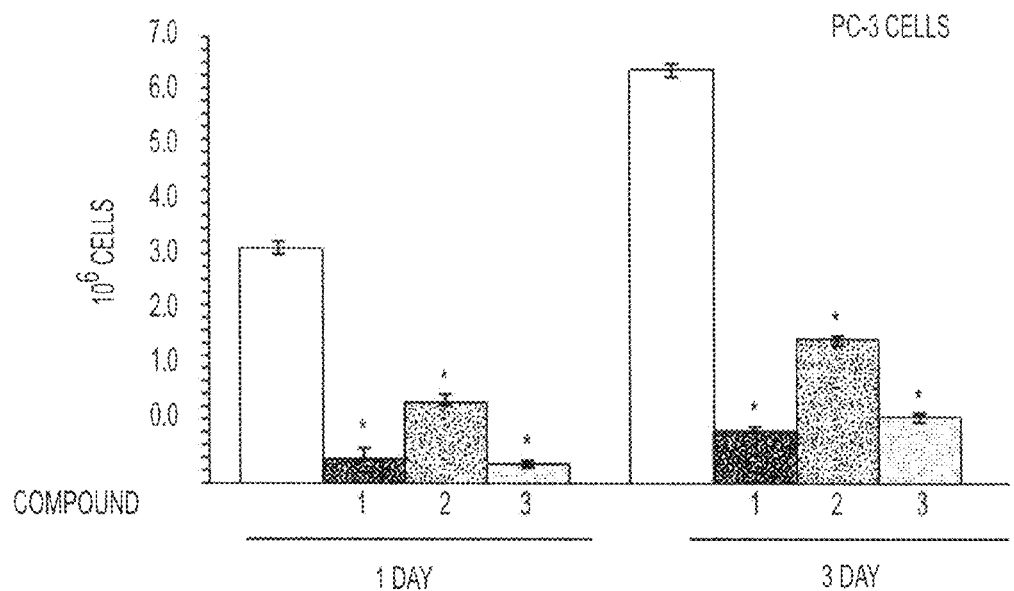
FIGS. 7A and 7B are bar graphs comparing the time-dependent antiproliferative effect of 10 μM Compounds 1, 2 and 3 on PC3 and SGC7901 cells, respectively, for 24 and 72 h using MTT assay where results were expressed as the mean, SD, *P<0.05.
Figure 7B:
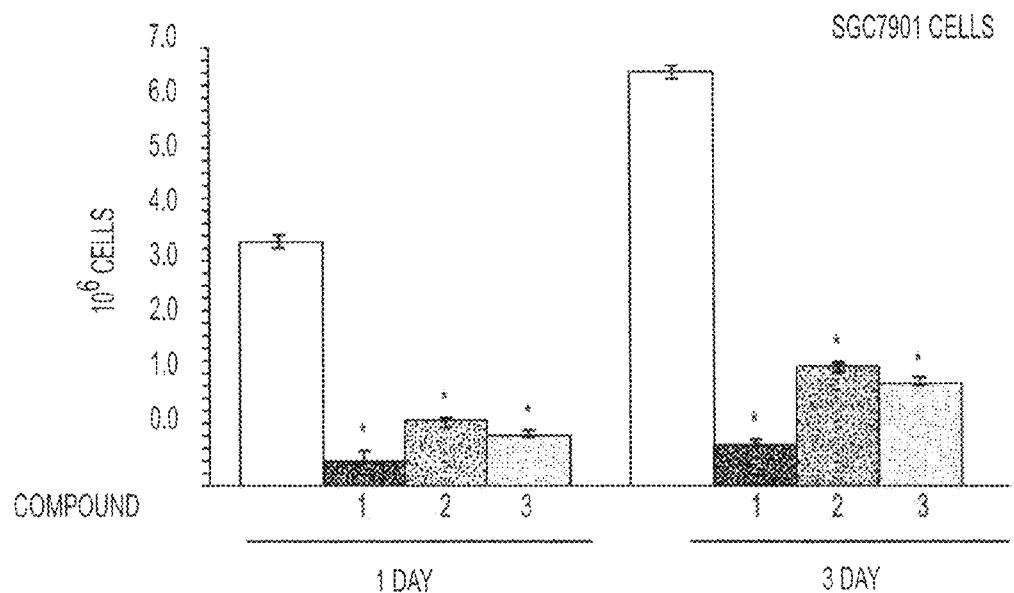

FIGS. 7A and 7B compare the time-dependent antiproliferative effects of 10 µM complexes 1, 2 and 3 on both PC3 and SGC7901 cancer cells for 24 and 72 h. It has been observed that the order of time dependent antiproliferative effect is complex 1>complex 3>complex 2 for both PC3 and SGC7901 cancer cells. Such comparative study leads to the conclusion that complex 1 may be the most effective antiproliferative agent among mixed ligand based gold(III) complexes 1-3.

The exact mechanisms on antiproliferation of [(DACH)Au(en)]Cl$_3$-type complexes on PC3 and SGC 7901 cancer cell lines remain unclear. The significantly diminished renal toxicity of ethylenediamine complex of gold(III) could be attributed to their different antiproliferative mechanism of action and selective sparing of the proximal tubular epithelial cells [Ahmed A, Al Tamimi D M, Isab A A, Alkhawajah A M M, Shawarby M A (2012) Histological changes in kidney and liver of rats due to gold(III) compound [Au(en)Cl$_2$]Cl. PLoS ONE 7:e51889—incorporated herein by reference in its entirety].

Most gold(III) compounds display reduced affinity for DNA and it seems reasonable that DNA is neither the primary nor the exclusive target for most gold(III) complexes. Recent studies have proposed a different mode of action for these compounds, in most of the cases, induce apoptosis was the mode of cell death [Vivek S, Kyoungweon P, Mohan S (2009) Colloidal dispersion of gold nanorods:

Historical background, optical properties, seed-mediated synthesis, shape separation and self assembly. Mater Sci Eng R 65:1-38; Niemeyer C M (2001) Nanoparticles, proteins, and nucleic acids: biotechnology meets materials science. Angew Chem Intl Ed 40:4128-4158; Pellegrino T, Kudera S, Liedl T, Javier A M, Manna L, Parak W J (2005) On the development of colloidal nanoparticles towards multifunctional structures and their possible use for biological applications. Small 1:48-63—each incorporated herein by reference in its entirety]. Their mechanism however, is not precisely delineated. However, the mechanisms associated with the inhibitory effects of complexes 1-3 on the proliferation of rapidly dividing cancer cells may be comprised of a cumulative impact on the induction of cell cycle blockage, interruption of the cell mitotic cycle, apoptosis (programmed cell death) and necrosis (premature cell death) [Taatjes D J, Sobel B E, Budd R C (2008) Morphological and cytochemical determination of cell death by apoptosis. Histochem Cell Biol 129:33-43; Takemura G, Minatoguchi M S, Fujiwara H (2013) Cardiomyocyte apoptosis in the failing heart—a critical review from definition and classification of cell death. Int J Cardio 167:2373-2386; Hayashi R, Nakatsui K, Sugiyama D, Kitajima T, Oohara N, Sugiya M, Osada S, Kodama H (2014) Anti-tumor activities of Au(I) complexed with bisphosphines in HL-60 cells. J Inorg Biochem 137:109-114—each incorporated herein by reference in its entirety].

Example 19

In Vitro Cytotoxicity of Gold(III Complexes 1-3 on Prostate (PC3) and Gastric (SGC7901) Cancer Cells Milovanovic et al. have studied the cytotoxicity studies of $[Au(en)Cl_2]^+$ and $[Au(SMC)Cl_2]^+$ where SMC=S-methyl-$_L$-cysteine and $[Au(DMSO)_2Cl_2]^+$ (DMSO=dimethyl sulphoxide). They concluded that gold(III) complexes are much faster to react with nucleophiles compare to Pt(II) complexes. They also demonstrated that gold(III) complexes exhibit relevant cytotoxic properties when tested on chronic lymphocytic leukemia cells (CLL). This conclusion indicates that gold(III) complexes have good potential for the treatment of cancer. In addition $[Au(en)Cl_2]^+$ complex shows cytotoxicity profiles comparable to cisplatin [Milovanovic M, Djekovic A, Volarevic V, Petrovic B, Arsenijevic N, Bugarcic Z D (2010) Ligand substitution reactions and cytotoxic properties of $[Au(L)Cl_2]^+$ and $[AuCl2(DMSO)_2]^+$ complexes (L=ethylenediamine and S-methyl-l-cysteine). J Inorg Biochem 104:944-949—incorporated herein by reference in its entirety]. In the present disclosure, a new series of gold(III) complexes 1-3 is developed by replacing two monodentate Cl$^-$ ligands with bidentate 1,2-DACH (1,2-diaminocyclohexane) ligand and subjected to in vitro cytotoxic evaluation against PC3 and SGC7901 cancer cell lines.

The in vitro cytotoxic effect of mixed ligand gold(III) diamine complexes against androgen-resistant prostate PC3 and human gastric SGC7901 cancer cells were studied using MTT assay. The in vitro cytotoxic activity depends on the exposure time and the concentration of complexes. For that reason, different concentrations and a 3-day exposure protocol were used in the present disclosure to determine the $IC_{50}$ values for all three complexes. The in vitro cytotoxicity in terms of $IC_{50}$ values of cisplatin for PC3 and SGC7901 cells was included for a comparison. The $IC_{50}$ data for the Au(III) complexes 1, 2 and 3 showed in vitro cytotoxicity in a wide range of 1.1-8.9 lM for PC3 cells, as given in Table 10. It can be seen from the $IC_{50}$ data for PC3 cancer cells that complex 1 showed ca. 100% and 50% better potency than complexes 2 and 3, respectively. It can be concluded that complexes 1 is relatively more effective cytotoxic agent than complexes 2 and 3). For PC3 cancer cells, the order of in vitro cytotoxicity in terms of $IC_{50}$ values is cisplatin (1.1 μM)>complex 1 (4.8 μM)>complex 3 (6.1 μM)>complex 2 (8.9 μM), as it is known that the lower the $IC_{50}$ value is, the higher the in vitro cytotoxicity.

All three complexes showed slightly lower potency vis-a-vis cisplatin. According to $IC_{50}$ data of monim-al-Mehboob et al., $[Au(en)_2]Cl_3$ with ethylenediamine ligands is a more prospective anti-cancer agent against prostate cancer PC3 cells. The dose dependent studies showed that $[Au(en)_2]Cl_3$ was found to execute a powerful and promising cytotoxic effect on PC3 cells which is comparable to that of cisplatin [Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of $[Au_2(pn)_2(Cl)_2]Cl_2.H_2O$. Polyhedron 61:225-234—incorporated herein by reference in its entirety]. For PC3 cells, $[Au(en)_2]Cl_3$ was recognized as effective cytotoxic agent as cisplatin while $[(en)AuCl_2]Cl$ showed almost 7-9 fold lower cytotoxicity as compared to cisplatin [Isab A A, Shaikh M N, Monim-ul-Mehboob M, Al-Maythalony B A, Wazeer M I M, Altuwaijri S (2011) Synthesis, characterization and antiproliferative effect of $[Au(en)_2]Cl_3$ and $[Au(N-propyl-en)_2]Cl_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of $[Au_2(pn)_2(Cl)_2]Cl_2.H_2O$. Polyhedron 61:225-234—each incorporated herein by reference in its entirety].

The $IC_{50}$ data for the Au(III) complexes 1, 2 and 3 showed in vitro cytotoxicity in the range of 5.5-7.9 lM for SGC7901 cells, as given in Table 10. It can be seen from the from $IC_{50}$ data for SGC7901 cancer cells that complex 1 showed comparable in vitro cytotoxicity to complex 3. Both complexes 2 and 3 are reasonably better cytotoxic agent than complex 3 For SGC7901 cancer cells, the order of in vitro cytotoxicity in terms of $IC_{50}$ values is complex 1 (5.5 μM)>complex 3 (5.8 μM)>cisplatin (7.3 μM)>complex 2 (7.9 μM). It is worth-mentioning that the in vitro cytotoxicity of both complexes 1 and 3 are fairly better than that of cisplatin.

For SGC7901 cells, $[Au(en)_2]Cl_3$ show slightly lower cytotoxicity with respect to cisplatin whereas $[(en)AuCl_2]Cl$ almost two fold more cytotoxic than cisplatin [Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of $[Au_2(pn)_2(Cl)_2]Cl_2.H_2O$. Polyhedron 61:225-234—incorporated herein by reference in its entirety]. $[(en)AuCl_2]Cl$ may be potential anti-cancer agents for cisplatin resistant SCG7901 cells [Isab A A, Shaikh M N, Monim-ul-Mehboob M, Al-Maythalony B A, Wazeer M I M, Altuwaijri S (2011) Synthesis, characterization and antiproliferative effect of $[Au(en)_2]Cl_3$ and $[Au(N-propyl-en)_2]Cl_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of [Au$_2$(pn)$_2$(Cl)$_2$]Cl$_2$.H$_2$O. Polyhedron 61:225-234—each incorporated herein by reference in its entirety]. An independent assessment of [Au(en)$_2$]Cl$_3$ and its derivatives reveals an interesting feature that SGC7901 gastric cancer cells exhibit 7-8 fold intrinsic resistance relative to the PC3 cancer cells with respect to cisplatin. On the contrary, the [Au(en)$_2$]Cl$_3$-type complexes may have the potential to overcome mechanisms inducing resistance to cisplatin, particularly in the gastric cancer SGC7901 cells [Isab A A, Shaikh M N, Monim-ul-Mehboob M, Al-Maythalony B A, Wazeer M I M, Altuwaijri S (2011) Synthesis, characterization and antiproliferative effect of [Au(en)$_2$]Cl$_3$ and [Au(N-propyl-en)$_2$]Cl$_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of [Au$_2$(pn)$_2$(Cl)$_2$]Cl$_2$.H$_2$O. Polyhedron 61:225-234—each incorporated herein by reference in its entirety]. Nevertheless, only two-fold or less resistance to the [Au(en)$_2$]Cl$_3$-type complexes was observed for PC3. This suggests that the intrinsic factors regulating cellular sensitivity to cisplatin and [Au(en)$_2$]Cl$_3$ are different for PC3 and SGC7901 cells. The factors affecting sensitivity of PC3 and SGC7901 towards cisplatin cells are analogous in the [Au(en)$_2$]Cl$_3$ type complexes [Isab A A, Shaikh M N, Monim-ul-Mehboob M, Al-Maythalony B A, Wazeer M I M, Altuwaijri S (2011) Synthesis, characterization and antiproliferative effect of [Au(en)$_2$]Cl$_3$ and [Au(N-propyl-en)$_2$]Cl$_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of [Au$_2$(pn)$_2$(Cl)$_2$]Cl$_2$.H$_2$O. Polyhedron 61:225-234—each incorporated herein by reference in its entirety]. These in vitro cytotoxicity results reveal that gold(III) complexes containing ethylenediamine and 1,2-diaminocyclohexane ligands are better anticancer agents than [Au(1,2-DACH)Cl2]Cl, [Au(1,2-DACH)$_2$]Cl$_3$; and [Au(en)$_2$]Cl$_3$ and its derivative complexes against gastric SCG7901 cancer cell line [Isab A A, Shaikh M N, Monim-ul-Mehboob M, Al-Maythalony B A, Wazeer M I M, Altuwaijri S (2011) Synthesis, characterization and antiproliferative effect of [Au(en)$_2$]Cl$_3$ and [Au(N-propyl-en)$_2$]Cl$_3$ on human cancer cell lines. Spectrochim Acta (A) 79:1196-1201; Monim-ul-Mehboob M, Altaf M, Fettouhi M, Isab A A, Wazeer M I M, Shaikh M N, Altuwaijri S (2013) Synthesis, spectroscopic characterization and anti-cancer properties of new gold(III)-alkanediamine complexes against gastric, prostate and ovarian cancer cells; crystal structure of [Au$_2$(pn)$_2$(Cl)$_2$]Cl$_2$.H$_2$O. Polyhedron 61:225-234—each incorporated herein by reference in its entirety]; Al-Maythalony B A, Wazeer M I M, Isab A A (2009) Synthesis and characterization of gold(III) complexes with alkyldiamine ligands. Inorg Chim Acta 362:3109-3113; Al-Jaroudi S S, Fettouhi M, Wazeer M I M, Isab A A, Altuwaijri S (2013) Synthesis and characterization and cytotoxicity of new gold(III) complexes with 1,2-diaminocyclohexane: influence of stereochemistry on antitumor activity. Polyhedron 50:434-442; Al-Jaroudi S S, Monim-ul-Mehboob M, Altaf M, Fettouhi M, Wazeer M I M, Isab A A (2014) Synthesis, spectroscopic characterization, X-ray structure and electrochemistry of new bis(1,2-diaminocyclohexane) gold(III) chloride compounds and their anticancer activities against PC3 and SGC7901 cancer cell lines. New J Chem 38:3199-3211)—each incorporated herein by reference in its entirety). According to IC$_{50}$ data presented herein, gold(III) complexes 1 and 3 were more effective than [Au(1,2-DACH)Cl$_2$]Cl against prostate PC3 cancer cells [Al-Jaroudi S S, Fettouhi M, Wazeer M I M, Isab A A, Altuwaijri S (2013) Synthesis, characterization and cytotoxicity of new gold(III) complexes with 1,2-diaminocyclohexane: influence of stereochemistry on antitumor activity. Polyhedron 50:434-442—incorporated herein by reference in its entirety].

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:
1. A gold(III) complex having Formula A:

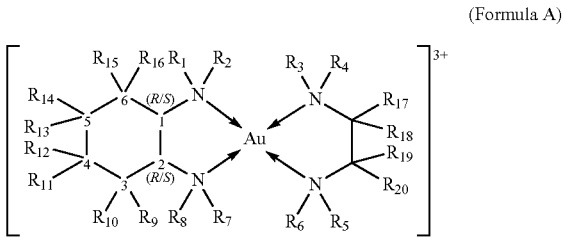

(Formula A)

or a pharmaceutically acceptable salt, ester, solvate or prodrug thereof;
wherein:
the complex has a cis- or trans-configuration;
1-6 each represents a carbon atom;
$R_1$-$R_8$ are each independently selected from the group consisting of a hydrogen atom; a linear or branched, substituted or unsubstituted $C_1$-$C_8$ alkyl group; and a substituted or unsubstituted $C_6$-$C_8$ aryl group; and
$R_9$-$R_{20}$ are each independently selected from the group consisting of a hydrogen atom, a halogen atom, a hydroxyl group a N-monosubstituted amino group, a N,N-disubstituted amino group, a substituted or unsubstituted $C_1$-$C_8$ alkyl group, a substituted or unsubstituted $C_1$-$C_8$ alkoxy group a substituted or unsubstituted $C_3$-$C_8$ cycloalkyl group, and a substituted or unsubstituted $C_6$-$C_8$ aryl group.

2. The gold(III) complex of claim 1, wherein:
$R_1$-$R_8$ are each independently selected from the group consisting of a hydrogen atom, a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted neopentyl group, a substituted or unsubstituted sec-pentyl group, a substituted or unsubstituted tert-pentyl group, a substituted or unsubstituted n-hexane group, a substituted or unsubstituted isohexane group, and a substituted or unsubstituted neohexane group; and $R_9$-$R_{20}$ are each independently a hydrogen atom, a halogen atom, a N-monosubstituted amino group, a N,N-disubstituted amino group, a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted isobutyl group, a substituted or unsubstituted sec-butyl group, a substituted or unsubstituted tert-butyl group, a substituted or unsubstituted n-pentyl group, a substituted or unsubstituted neopentyl group, a substituted or unsubstituted sec-pentyl group, a substituted or unsubstituted tert-pentyl group, a substituted or unsubstituted n-hexane group, a substituted or unsubstituted isohexane group, and a substituted or unsubstituted neohexane group.

3. The gold(III) complex of claim 1, having a formula selected from the group consisting of Formula 1a, Formula 1b, Formula 2a and Formula 2b:

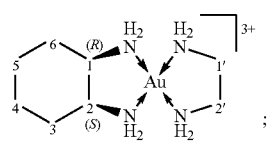

Formula 1a

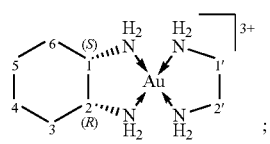

Formula 1b

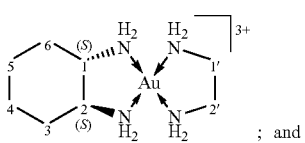

Formula 2a

; and

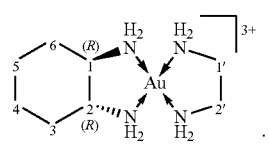

Formula 2b

.

4. The gold(III) complex of claim 1, further comprising one or more pharmaceutically acceptable anions selected from the group consisting of fluoride, chloride, bromide, iodide, nitrate, sulfate, phosphate, amide, methanesulfonate, ethanesulfonate, p-toluenesulfonate, salicylate, malate, maleate, succinate, tartarate, citrate, acetate, perchlorate, trifluoromethanesulfonate, acetylacetonate, hexafluorophosphate, and hexafluoroacetylacetonate.

5. A composition, comprising:
    the gold(III) complex of claim 1 or a pharmaceutically acceptable salt, ester, solvate or prodrug thereof; and
    one or more pharmaceutically acceptable carriers.

6. The composition of claim 5, further comprising one or more other active pharmaceutical agents.

7. The composition of claim 5, wherein the composition is in solid, semi-solid or liquid dosage forms.

8. The composition of claim 5, wherein the composition is formulated for one or more modes of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

9. A method for treating one or more types of cancer in a mammalian subject in need thereof, comprising:
    administering a therapeutically effective amount of the composition of claim 5 to the mammalian subject; wherein the one or more types of cancer are prostate cancer and/or gastrointestinal cancer.

10. The method of claim 9, wherein the therapeutically effective amount comprises 5-50 μM of the gold(III) complex or a pharmaceutically acceptable salt, ester, solvate or prodrug thereof.

11. A method for inhibiting proliferation of cancer cells, comprising:
    contacting the cancer cells with the gold(III) complex of claim 1 or a pharmaceutically acceptable salt, ester, solvate or prodrug thereof; wherein the cancer cells are prostate cancer cells and/or gastrointestinal cancer cells.

12. The method of claim 11, wherein the cancer cells are human cells.

13. The method of claim 11, wherein the gold(III) complex has a concentration of 5-50 μM.

14. The method of claim 11, wherein the gold(III) complex exhibits an $IC_{50}$ of 1-20 μM for inhibiting the proliferation of the prostate cancer cells and/or the gastrointestinal cancer cells.

* * * * *